(12) United States Patent
Mandler et al.

(10) Patent No.: US 6,275,150 B1
(45) Date of Patent: Aug. 14, 2001

(54) USER INTERFACE FOR A BIOMEDICAL ANALYZER SYSTEM

(75) Inventors: Alan Mandler, Los Angeles; Marsh Chamberlain, Granite Bay, both of CA (US); Gary L. Allen, Monroe, NY (US); Luis De Luzuriaga, Wilton, CT (US); Donald J. Kennel, Pomona, NY (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/115,129

(22) Filed: Jul. 14, 1998

(51) Int. Cl.[7] .................................................. G08B 25/00
(52) U.S. Cl. .......................... 340/525; 340/506; 340/521; 340/524; 340/825.36; 340/825.49
(58) Field of Search ..................................... 340/506, 517, 340/521, 524, 525, 825.36, 825.49

(56) References Cited

U.S. PATENT DOCUMENTS 5,396,224 * 3/1995 Dukes et al. .................... 340/825.49
5,896,086 * 4/1999 Ida .................................... 340/524

* cited by examiner

*Primary Examiner*—Daryl Pope
(74) *Attorney, Agent, or Firm*—Andrew L. Klawitter; John M. Paolino

(57) ABSTRACT

A user interface for use on the computer of a biomedical analyzer system having at least one biomedical analyzer instrument. The user interface inputs work orders, including sample and test id's, and transmits them to the instrument. The instrument performs the requested tests and sends the results to the computer, where they are stored. The test results are compared to exception review criteria to identify exception test results for operator review. Exception test results are indicated by a graphic icon on the display of the computer. The exception test results are compared by an operator to validation data gathered from the instrument and stored in the computer. The operator may then select a disposition for the exception test results. Alarm conditions are communicated by the instrument to the computer and the user interface communicates the alarm conditions to an operator by using a graphic image of the instrument and an affected part.

42 Claims, 26 Drawing Sheets

LEGEND
▨ = RED

RECORDS MANAGEMENT: OVERVIEW

| SELECT | NAME | PATIENT ID | SAMPLE ID | STATUS | TYPE | ORDER D/T | PRIORITY |
|---|---|---|---|---|---|---|---|
| ☐ | ORENSTEIN, ETHEL 1235678 | 12345678901234567890 | 00000000000000316001 | X | SERUM | 01/11/98 06:45 | STAT |
| ☐ | | | 00000000000000316002 | IP | CSF | 01/12/98 06:45 | STAT |
| ☐ | HARMON, ELIXABETH 345890 | 12345678901234567890 | 12345678901234567890 | X | SERUM | 01/12/98 06:50 | STAT |
| ☐ | CRANFORD, JAMES 90 | 12345678901234567890 | 12345678901234567890 | X | SERUM | 01/12/98 06:51 | STAT |
| ☐ | ORENSTEIN, ETHEL 7890 | 12345678901234567890 | 12345678901234567890 | X | SERUM | 01/12/98 06:52 | RERUN |
| ☐ | WELLSLEY, GERALD | 12345678901234567890 | 00000000000000320001 | X | SERUM | 01/12/98 06:53 | RERUN |
| ☐ | | | 00000000000000320002 | C | URINE | 01/12/98 06:53 | |
| ☐ | CARLINO, JANE COLLEEN | 12345678901234567890 | 12345678901234567890 | X | CSF | 01/12/98 06:55 | RERUN |
| ☐ | ORTHO CC LEVEL 1 | 00000000000008501001 | 12345678901234567890 | X | | 01/11/98 06:56 | CTL |
| ☐ | MILLER, SCOTT | 12345678901234567890 | 12345678901234567890 | X | SERUM | 01/11/98 06:57 | |
| ☐ | WELLSLEY, MADELLINE | 12345678901234567890 | 12345678901234567890 | X | URINE | 01/11/98 06:58 | |
| ☐ | SMITH, JAMES KRAMER | 12345678901234567890 | 12345678901234567890 | P | PLASMA | 01/12/98 06:59 | |
| ☐ | CRANFORD, JAMES | 12345678901234567890 | 12345678901234567890 | X | URINE | 01/11/98 07:00 | |
| ☐ | CUPALUOLO, CHRISTINE | 12345678901234567890 | 12345678901234567890 | X | PLASMA | 01/12/98 07:02 | |
| ☐ | DEMARCO, ANTHONY | 00000000000008501001 | 12345678901234567890 | C | URINE | 01/11/98 07:05 | |
| ☐ | DUGAL, ARTHUR | 12345678901234567890 | 12345678901234567890 | C | URINE | 01/12/98 07:06 | |
| ☐ | EBERHARDT, ALFRED | 12345678901234567890 | 12345678901234567890 | C | URINE | 01/11/98 07:08 | |
| ☐ | FAHEY, JOHN | 12345678901234567890 | 12345678901234567890 | C | PLASMA | 01/12/98 07:10 | |
| ☐ | GALLO, ERNEST JULIO | 00000000000008501001 | 12345678901234567890 | P | SERUM | 01/12/98 07:11 | |
| ☐ | GILMAN, BENJAMIN | 12345678901234567890 | 12345678901234567890 | C | SERUM | 01/12/98 07:12 | |
| ☐ | GREIGER, CHARLES | 12345678901234567890 | 12345678901234567890 | IP | URINE | 01/11/98 07:15 | |
| ☐ | HARMON, ELIXABETH | 12345678901234567890 | 12345678901234567890 | C | PLASMA | 01/12/98 07:20 | |
| ☐ | HEALEY, CHARLENE | 00000000000008501001 | 12345678901234567890 | C | SERUM | 01/12/98 07:21 | |

SELECT NAME TO ACCESS DETAILS

OVERVIEW | DETAILS | RECORDS | SUMMARY | WORK ORDER | METHOD | PENDING | IN PROCESS | EXCEPTIONS | COMPLETE | HISTORICAL | COMPOSITE | SEARCH | EXPAND ROWS | SORT BY: ORD D/T | FILTER: LOC | FILTER: DOCTOR | FILTER: PRIORITY

RESET TO PENDING | OPEN EXCEPTIONS | PURGE | PRINT

FIG. 9A

EXCEPTION REVIEW CRITERIA PARAMETERS
REVIEW
- ☐ REVIEW NONE
- ☐ REVIEW ALL
- ☑ REVIEW BY EXCEPTION

| YES | NO | |
|---|---|---|
| ☑ | | INSTRUMENT FLAGS |
| ☑ | ☐ | RANGE FAILURES: |

LEVEL:
- ☐ < > NORMAL
- ☑ >= VERY HIGH OR <= VERY LO
- ☐ >= PANIC HIGH OR <= PANIC LO

| YES | NO | |
|---|---|---|
| ☑ | ☐ | EXCEEDS DILUTION THRESHOLD |
| ☑ | ☐ | DELTA CHECK FAILURES |
| ☑ | ☐ | ALERT VALUES: |
| ☑ | ☐ | SAMPLES AFTER A CONTROL FAILURE |
| ☑ | ☐ | SAMPLES AFTER A PATIENT MEAN FAILURE |
| ☑ | ☐ | REFLEX CASCADE TRIGGERED |
| ☐ | ☑ | STAT SAMPLES |

AUTO RERUN

| YES | NO | |
|---|---|---|
| ☑ | ☐ | INSTRUMENT FLAGS |
| ☑ | ☐ | RANGE FAILURES |
| ☑ | ☐ | EXCEEDS DILUTION THRESHOLD |
| ☑ | ☐ | # OF AUTO DILUTIONS BEFORE HOLD: |

- ☐ 1
- ☑ 2
- ☐ 3

| YES | NO | |
|---|---|---|
| ☑ | ☐ | DELTA CHECK FAILURES |
| ☐ | ☑ | ALERT VALUES |
| ☑ | ☐ | PERFORM REFLEX METHOD(S) CASCADE |

HOLD FOR FINAL REVIEW

| YES | NO | |
|---|---|---|
| ☐ | ☑ | SAMPLES THAT HAD AN INSTRUMENT FAILURE |
| ☑ | ☐ | SAMPLES THAT HAD A RANGE FAILURE |
| ☐ | ☑ | SAMPLES THAT HAD BEEN DILUTED 'N' TIMES |
| ☐ | ☑ | SAMPLES THAT HAD A DELTA CHECK FAILURE |
| ☑ | ☐ | SAMPLES THAT HAD AN ALERT VALUE |
| ☑ | ☐ | SAMPLES THAT HAD A CONTROL FAILURE |
| ☑ | ☐ | SAMPLES THAT HAD A PATIENT MEAN FAILURE |
| ☑ | ☐ | SAMPLES THAT HAD REFLEX TESTING |

☐ ACCEPT    CLEAR

USER INTERFACE FOR A BIOMEDICAL ANALYZER SYSTEM

FIELD OF THE INVENTION

The present invention relates to a user interface for a biomedical analyzer system. More particularly, the present invention relates to a fully integrated graphic user interface (GUI) for a biomedical analyzer system.

BACKGROUND OF INVENTION

Presently, almost every medical laboratory has some form of a Laboratory Information System (LIS) to collect and manage patient test data. To date, however, no emphasis has been placed on developing such systems to operate in a manner that is user friendly or intuitive. To the contrary, they have typically been difficult to operate, requiring the operator to be familiar with many commands and procedures. For example, when analyzing patient test data, the operator was required to manually validate test results by manually checking exceptions against historical instrument performance and/or patient data. Thus, much of the validation process was left to individual operator discretion and experience.

Recently many medical laboratories have added Laboratory Automation Systems (LAS) to control the processing of biological samples. Again, however, these systems have not been particularly user friendly, for example, only providing error messages rather than directing the user to take appropriate corrective action. In addition, when present, the LAS has in the past been operated as an independent system from the LIS, providing little or no integration. Further, many systems required individual control systems for each biomedical analyzer instrument. Thus, laboratories having more that one instrument required multiple, independent controls.

SUMMARY OF THE INVENTION

It is, therefore, an object of the present invention to provide a user friendly GUI for a biomedical analyzer system.

Another object of the present invention is to provide an integrated LIS and LAS for use in a biomedical laboratory.

A further object of the present invention is to provide a simple means for validating exceptions in patient sample data.

Yet another object of the present invention is to provide a graphical alarm system for use with a biomedical analyzer system.

The above and other objects are achieved in accordance with a first aspect of the present invention by a user interface for use on the computer of a biomedical analyzer system having at least one biomedical analyzer instrument. The user interface inputs work orders, including sample and test id's, and transmits instructions to the instrument. The instrument performs the requested tests and sends the results to the computer, where they are stored. The test results are compared to exception review criteria to identify exception test results for operator review. Exception test results are also indicated by a graphic icon on the display of the computer. The exception test results may be compared by an operator to validation data gathered from the instrument and stored in the computer. The operator may then select a disposition for the exception test results.

In another aspect of the present invention, alarm conditions are communicated by the instrument to the computer. The user interface then communicates the alarm conditions to an operator by using a graphic image of the instrument and an affected part. Additional information may then be provided to the operator by selecting the affected component.

These and other objects, features and advantages of the present invention will be apparent and fully understood from the following detailed description of the preferred embodiments, taken in connection with the appended drawings.

BRIEF DESCRIPTION OF THE DRAWINGS

FIG. 9A is an illustration of the Records floating window display of the present invention with the Overview and Records slides engaged.

FIG. 12 is an illustration of the Exception Review Criteria Parameter definition screen of the present invention.

FIG. 14 is an illustration of the Exceptions floating window of FIG. 13 with the By Method menu displayed.

FIG. 20 is an illustration of the Exceptions floating window display of the present invention with the Details and Validation slides engaged.

DETAILED DESCRIPTION OF THE PREFERRED EMBODIMENT

Figure 1:
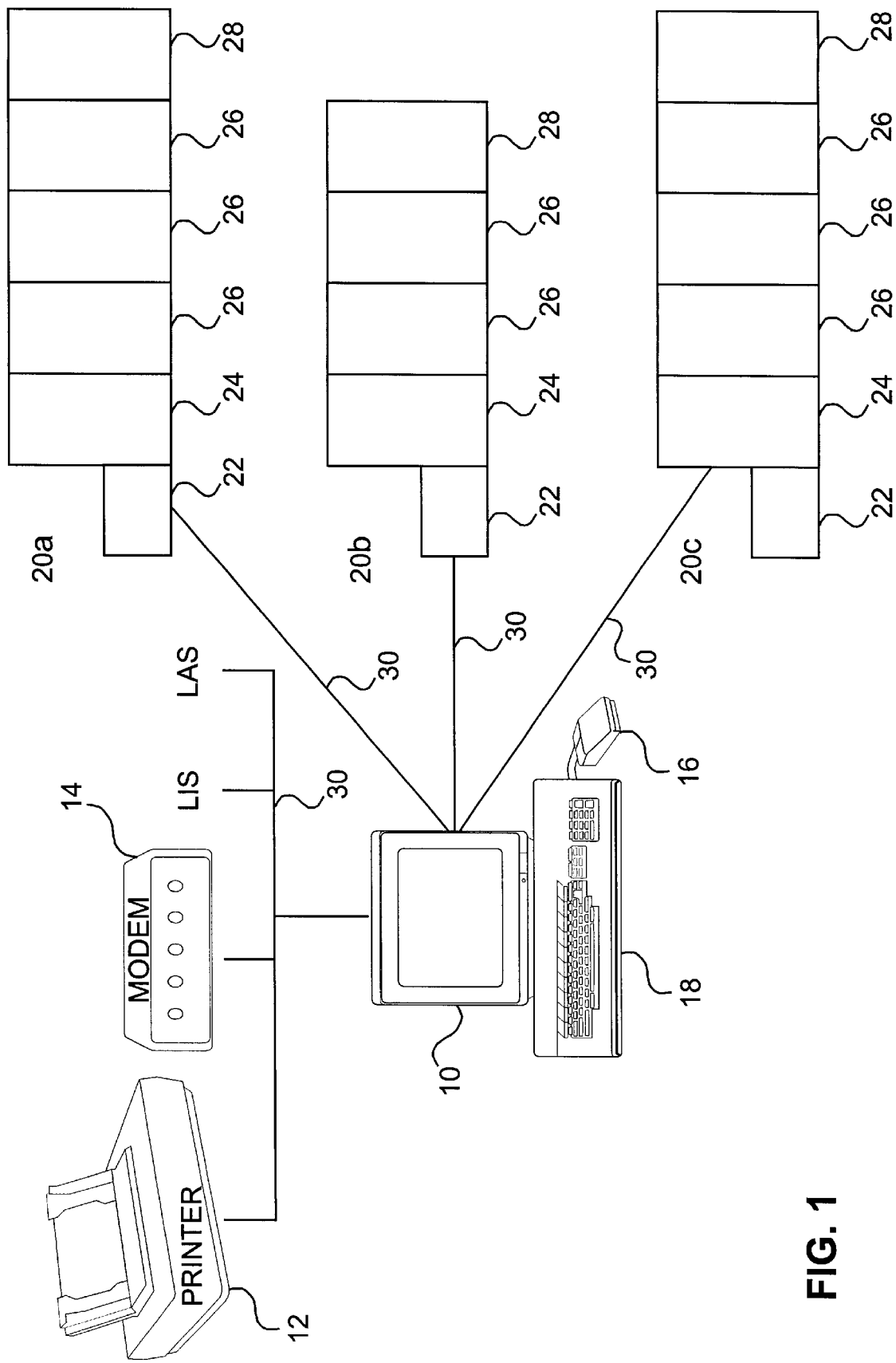
FIG. 1 is an illustration of a biomedical analyzer system according to the present invention.

Referring first to FIG. 1, a biomedical analyzer system 1 according to the present invention is illustrated. The illustrated system includes three Advia modular biomedical analyzer instruments 20a–20c, the associated host computer 10 and the related network connections 30, all of which are marketed by Bayer Corp. The host computer 10 of the illustrated embodiment is a standard IBM compatible personal computer having a Super VGA display monitor, a Pentium® central processing unit (CPU) and a data storage system including ROM, RAM, hard disk and CD memories. The network connection 30 between the host computer 10 and Advia instruments 20a–20c is an Ethernet network. Through this network 30, the host computer 10 sends command messages to the instruments 20a–20c, which include commands affecting the function of the instrument (e.g., change state from ready to stand-by) and commands directing that tests be performed. The instruments 20a–20c can likewise send messages to the host computer 10 via the network 30, such as test results, error and alarms messages. The host computer 10 is also connected to a printer 12 and modem 14, as well as the LIS and LAS, either directly or through the network 30. It should, however, be apparent to one of ordinary skill in the art, given the present disclosure, that other computers having different displays, processing means and data storage systems may be employed. Further, although the host computer 10 is illustrated as a separate physical component, electrically connected to the instruments, it may be incorporated into one of the instruments or located at a remote location and linked to the instruments though other communication means, such as a LAN, telephone lines, fiber optics, infra-red or radio transmission.

Each Advia instrument 20a–20c is an integrated modular instrument that includes a base module that contains a sampler module 22 and a pre-dilution/ISE module 24, and up to four analyzer modules. The analyzer modules are selected from two types of analyzer modules, chemistry modules 26 and immuno-assay modules 28. It should be noted that the number of instruments and the exact configuration of each instrument is a matter of choice depending on the testing and throughput requirements of the individual lab. It should also be noted that other modules, and instruments (modular or non-modular) other than Advia instruments may be used and still be within the scope of the present invention.

The sampler module 22 is the input for samples to be analyzed. It receives samples from an operator and delivers them, as directed by the host computer 10, to the other modules where the requested tests are performed. The pre-dilution/ISE module 24 performs any pre-treatment or pre-dilution of the samples as required. The pre-dilution/ISE module 24 also performs Ion Selectable Electrode (ISE) testing when requested. The chemistry and immuno-assay modules 26 and 28 perform chemical and immuno-assay testing of the samples, respectively.

Figure 2:
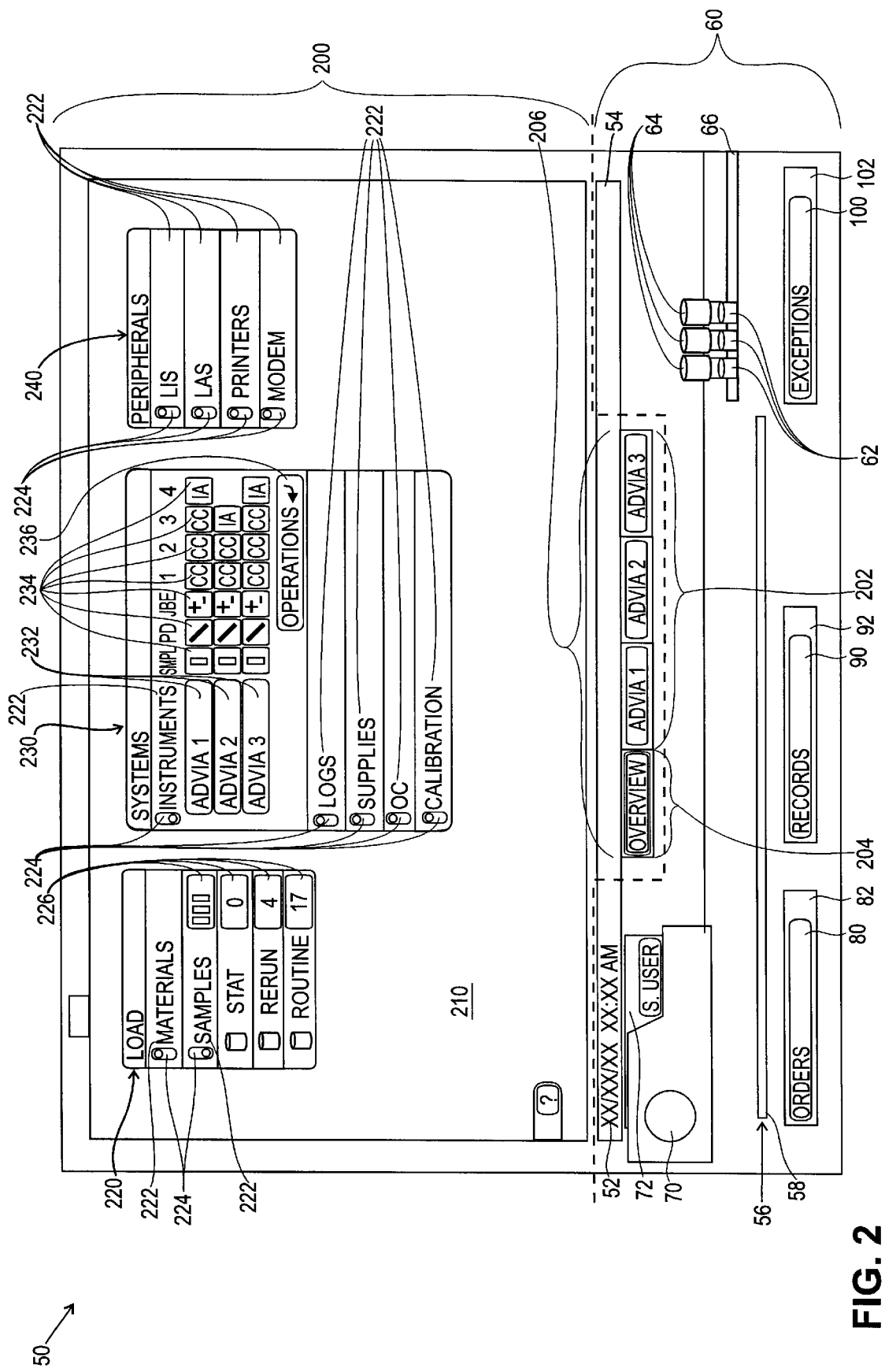
FIG. 2 is an illustration of the main screen of the GUI of the present invention with the overview display in the system management window.

As indicated above, the host computer 10 includes a software package that integrates the LIS and LAS. The computer 10 is, therefore, able to both control operation of the instruments, and collect, analyze and store the resulting data. FIG. 2 illustrates the main screen 50 of the graphic user interface (GUI) of the host computer's software package. The screen is divided into two areas, the upper system management window 200, which includes equipment related information, and the lower data management desktop 60, which includes patient and quality control (QC) related information. The user interface uses a mouse 16 and a keyboard 18 as the primary input devices and uses input conventions similar to other Windows™ based applications, for example, switches, buttons and check boxes, the use of which is well known to those of ordinary skill in the art. It should be noted, however, that other common input devices (e.g. light pens, touch screens and hand held scanners) and other communication conventions may be used.

Figure 3:
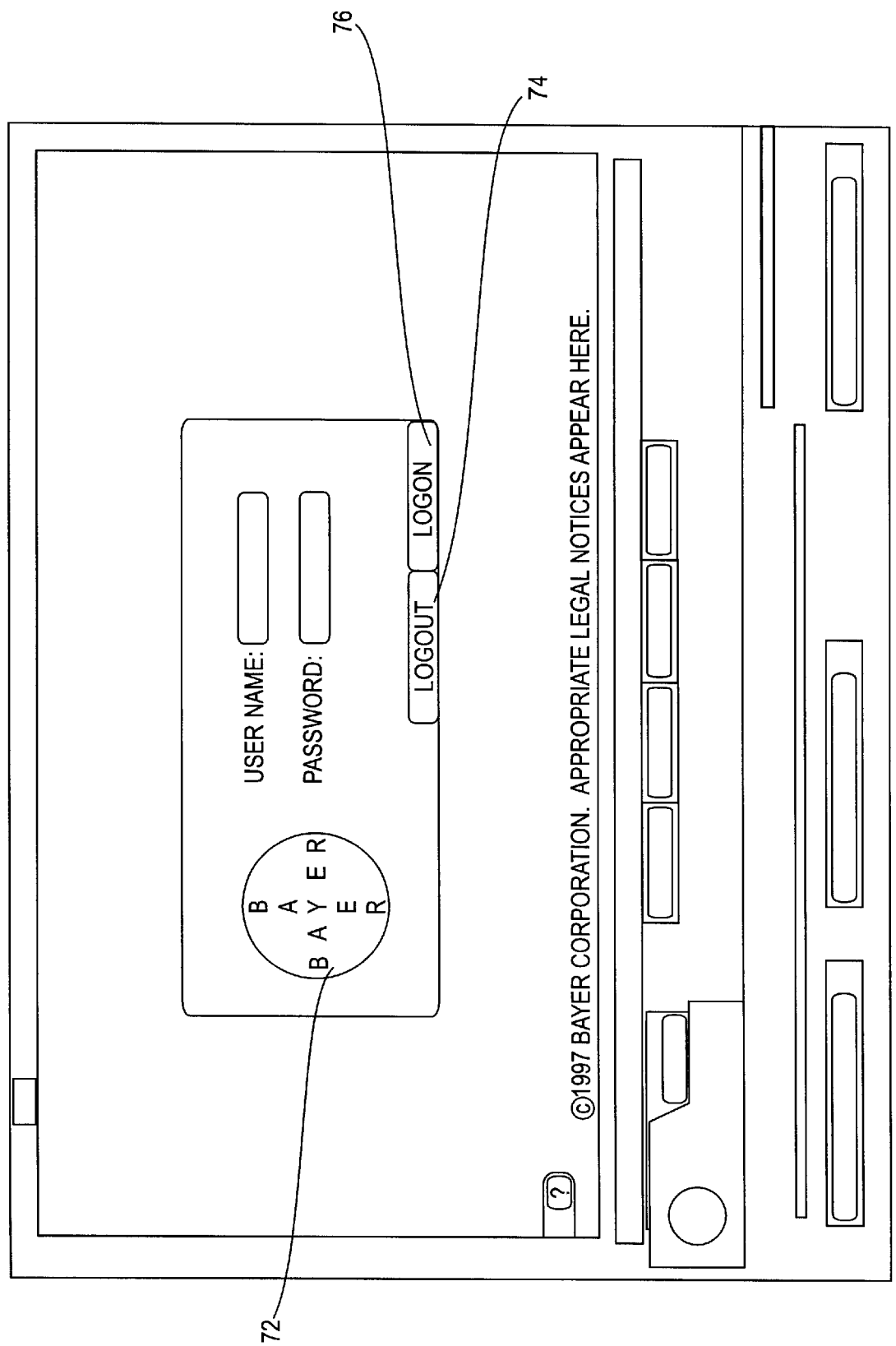
FIG. 3 is an illustration of the login screen of the GUI of the present invention.

Located on the left side of the data management desktop 60 is an id badge icon 72. To log in to the system, a user enters his or her user name and password on the id badge icon 72. This is done by clicking on the id badge 72 to "eject" it from its slot 70 (FIG. 3) and entering the appropriate data. The user then clicks on the Login button 74 on the id badge 72 to return it to the slot 70 and to return to the main GUI screen 50. To log out, the user would merely click on Logout 76, rather than Login 74, after ejecting the id badge 72. Depending on an individual user's access rights, different regions of the data management desktop 60 and system management window 200 (as well as other screens described herein) will be dimmed or absent, indicating the associated function is inactive or unavailable to that user. In addition, in certain instances, the user may be able to view data and instrument status, but will not have access to create or edit the data or change instrument status.

There are three message areas 52, 54, 56 on the main GUI screen which are used to convey information to a user. In the embodiment illustrated in FIG. 2, the first area 52 communicates information regarding the individual session and user (e.g., user id, date and time) and the second area 54 communicates information regarding the processing of any tests (e.g., three exceptions). A message tablet pops up from a slot 58 in the third area 56 to communicate any prompting or progress messages.

System Management Window

Figure 4:
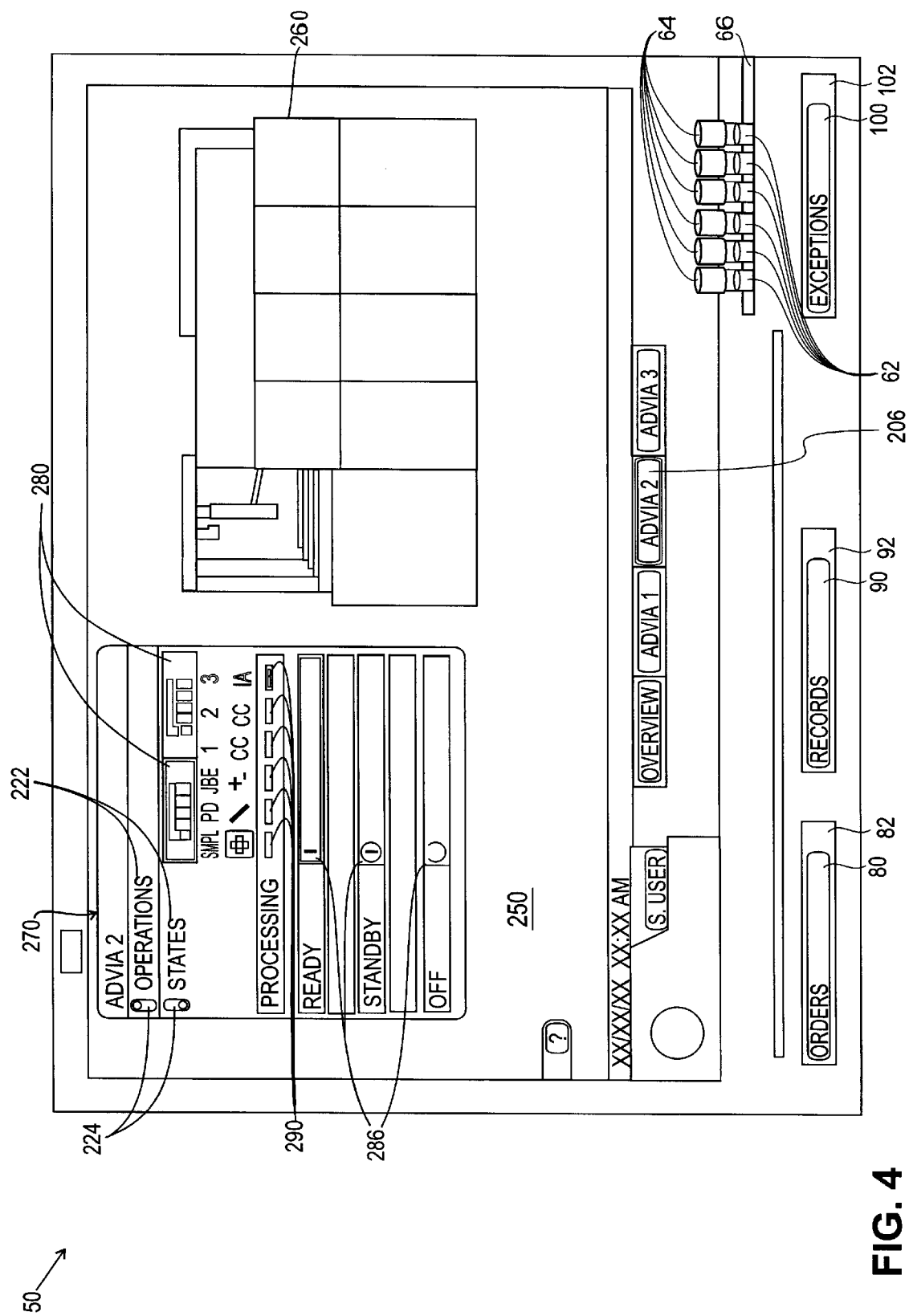
FIG. 4 is an illustration of the main screen of the GUI of the present invention with the instrument specific display in machine view mode in the system management window.

The system management window 200, i.e., the upper area of the main GUI screen (FIG. 2), is intended to convey the actual workings of the lab's equipment requirements and operations. As shown in FIG. 2, this relates to loading and unloading of samples, machine and module status, calibration, maintenance, and peripheral status. Just below the system management window 200 are a series of instrument selection buttons 202, which control what is displayed in the system management window 200. The first button is the Overview button 204, used to engage the overview display 210 (FIG. 2). The remaining buttons are instrument specific buttons 206, used to engage the instrument specific display 250 (FIG. 4). The number of instrument buttons 206 varies depending on the number of Advia or other compatible instruments connected to the system. If none of the instrument selection buttons 202 are engaged, the system management window 200 with the most recent display is dimmed indicating no selections are active.

The overview display 210, shown in FIG. 2, has three primary menus called panels, the Load panel 220, the Systems panel 230 and the Peripherals panel 240. The Load panel 220 controls and displays information relating to loading and unloading of samples to be tested and materials (e.g., reagents). The System panel 230 controls and displays information relating to instrument and module status, including, calibration, QC, supplies, and logs. The Peripheral panel 240 controls and displays information relating to the LIS and LAS, as well as any peripherals attached to the system (e.g., printers and modems).

Within each panel 220, 230, 240 are individual sections 222, for example, in the Load panel 220 there is a Materials section and a Samples section. To the left of each section 222 is a toggle switch 224. When a switch 224 is in its upper position, the corresponding section 222 and its contents are hidden. When the switch 224 is moved to the lower position (engaged), the contents of the section 222 are displayed. Referring to FIG. 2, the toggle switches 224 for the Samples section of the Load panel 220 and the Instruments section of the Systems panel 230 are engaged, thereby displaying the contents of those sections. Due to display size restraints, only one toggle switch 224 in each panel may be engaged at any one time. Thus, engaging a switch 224 will automatically disengage any other switch 224 in that panel. This also helps keep the user focused on the selected section.

Opening a section 222 provides access to a number of buttons, which may be activated to obtain further information or to access other functions. Within each of the sections 222 of the Systems panel 230, it may be seen that there is a button 232 for each instrument, as well as individual component buttons 234 for each component of each instrument. From left to right, the component buttons 234 in the illustrated embodiment are sampler, pre-dilution, ISE, one or more chemistry modules and one or more immuno-assay modules. Although pre-dilution and ISE are physically one module in the Advia instrument, they are treated individually as separate components. There is also a command button 236 located at the bottom of each section 222. The command activated by the command button 236 varies depending on the section 222 and the button(s) selected within the section.

The Load and Peripherals panels 220, 240 provide access to information and control of the corresponding items. For example, within the Samples section of the Load panel 220 are a number of buttons 226 which provide access to the Orders floating window 80 (described below). The top button accesses all orders, the second accesses orders for stat samples only, the third accesses rerun orders only and the last button access routine orders only. In addition, each of the lower three buttons indicate the number of orders that exist for each type of order. As described below, the Orders floating window 80 allows the user to view and modify pending orders, as well as create new orders.

When one of the instrument specific instrument selection buttons 206 are engaged, the instrument specific display 250, shown in FIG. 4, replaces the overview display 210. The instrument specific display 250 includes a graphical representation of the instrument 260 corresponding to the selected button 206, an Advia instrument in the illustrated example. On the left side of the instrument specific display 250 is an Instrument panel 270 having two sections 222, an Operation section and a States section, which are used to control and display information relating to the selected instrument.

Figure 5:
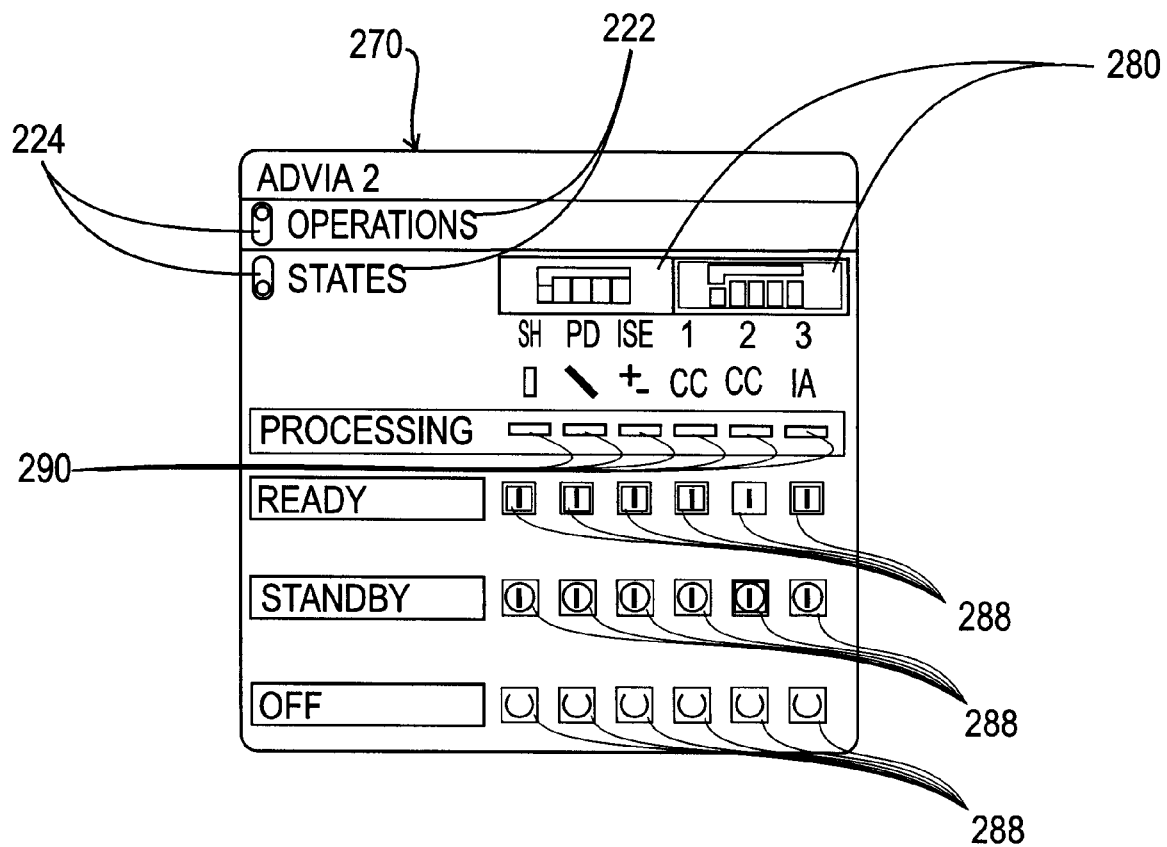
FIG. 5 is an illustration of the main screen of FIG. 4 with the instrument specific display in component view mode.
Figure 6A:
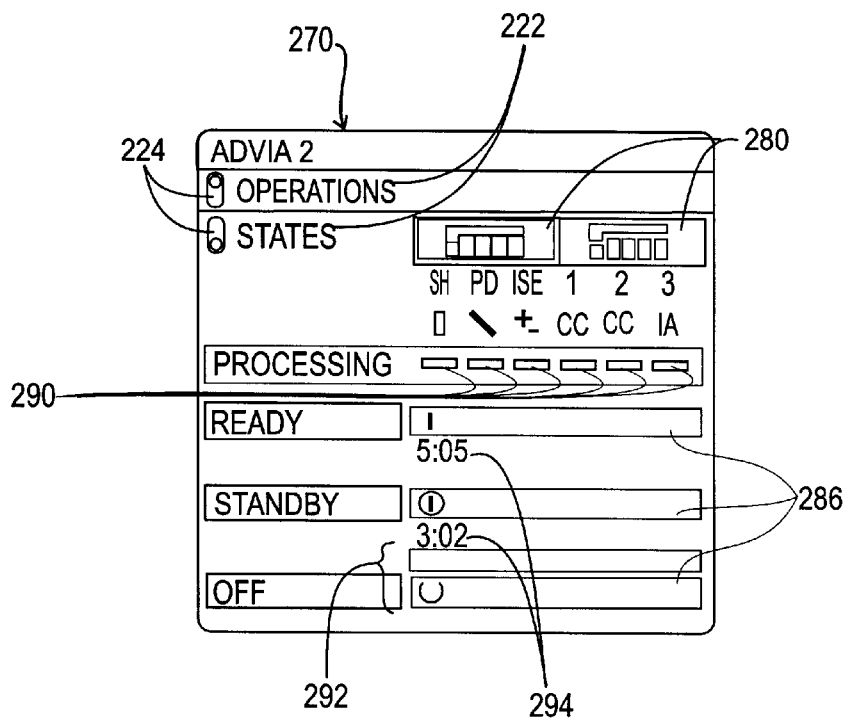
FIGS. 6A–6D illustrate the main screen of FIG. 4 with a progress bar and countdown timers.
Figure 6B:
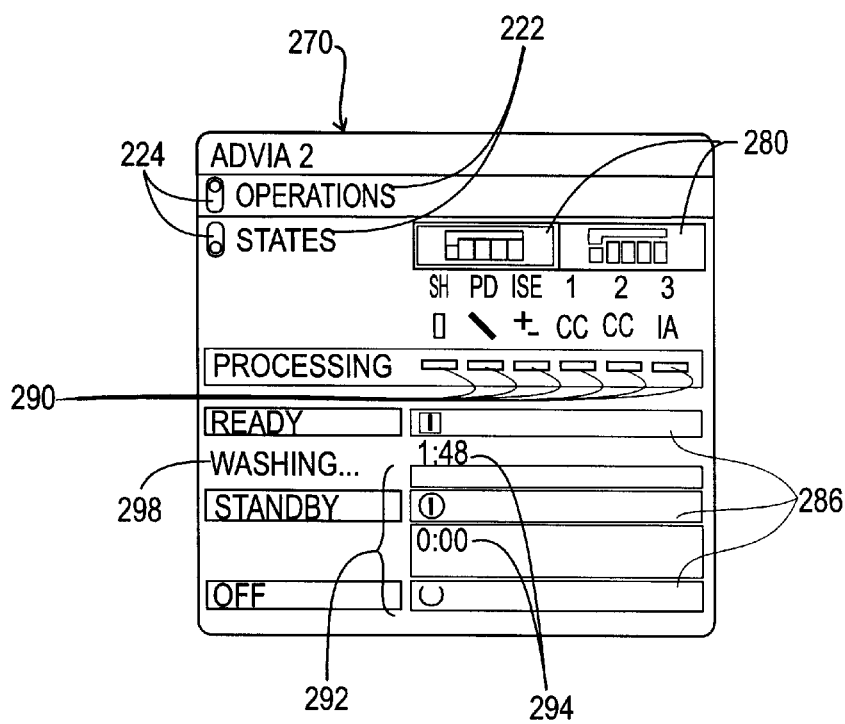
Figure 6C:
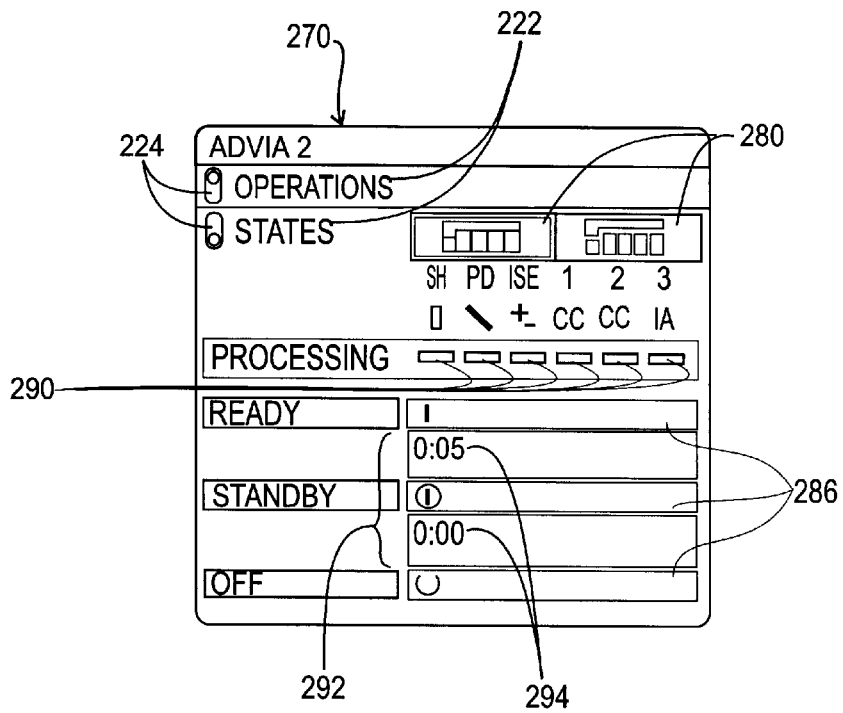
Figure 6D:
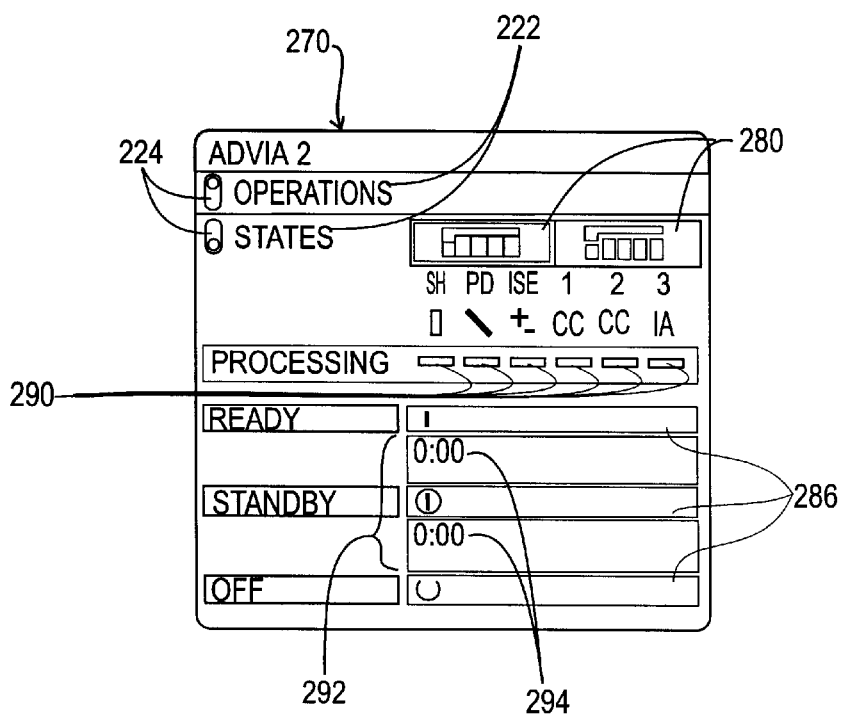

In addition to the toggle switches 224 previously described, each section 222 of the Instrument panel 270 also includes a pair of focus buttons 280 at the top when the section 222 is selected by the toggle switch 224. The focus buttons 280 switch the Instrument panel 270 between machine view (FIG. 4) and component view (FIG. 5). In both views, each component of the instrument is represented in the Instrument panel 270 by an individual column. Information regarding the components (e.g., current state) is displayed under the component identifiers and buttons control their operation. In the machine view (FIG. 4) a single machine button 286 extends across all the component columns to simultaneously control all the modules of an instrument. In the component view (FIG. 5), each component of each instrument has its own button 288 so that each component may be controlled independently. For example, in FIG. 4, the machine view focus button 280 is engaged (and backlit to so indicate) and the ready machine button 286 has been pressed, switching all the modules of the instrument to the ready state. The ready button 286 is backlit to indicate that the instrument is in the ready state. If components reach the ready state at different times, this may be indicated by backlighting different regions of the ready button 286 at the appropriate times. Turning to FIG. 5, the component view focus button 280 has been engaged thereby causing the machine control buttons 286 of FIG. 4 to be replaced by individual component control buttons 288 with one button 288 for each component of the instrument. In FIG. 5, one of the chemistry modules has been switched from the ready state to the standby state by engaging the appropriate component button 288. This button 288 is backlit to indicate that the component has achieved the desired state. Optionally, component buttons 288 and portions of machine buttons 286 may be backlit in different colors to communicate alarm conditions.

Above the machine (or component) buttons 286 (288) is a row of component status indicators 290 which are activated by the system to indicate when a component is busy processing a sample. Also, in addition to backlighting the machine (or component) buttons 286 (288) to indicate that a state has been achieved, progress bars 292 and/or countdown timers 294 may be used during the switching of states. As shown in FIGS. 6A–6D, the progress bar 292 extends from the previous state, to the selected state as the component reaches the desired state. For example, in FIG. 6A the system is switching between the Off and Standby state and in FIG. 6B the system has completed the transition to Standby and is in the process of switching to the Ready state. It should also be noted that in FIG. 6B a progress status message 298 is displayed between the Standby and Ready machine buttons 286 to communicate to the user more information regarding the status of the transition between states, in this case "Washing." Countdown timers 294 positioned between buttons 286 indicate the time remaining before the corresponding change in state is achieved. For example, in FIG. 6B the bottom countdown timer 294 displays "0:00" indicating that the Standby state has been achieved and the top timer 294 displays "1:48" indicating that it will be approximately one minute and 48 seconds until the Ready state is achieved.

One of the many advantages of the present invention is the ability to effectively communicate alarms to a user and direct the appropriate corrective action. Whenever a problem occurs that is instrument specific, the instrument sends an alarm message to the computer 10 by way of the network system 30. Alternative methods of communicating the alarm condition, including the use of interrupts or polling, may be used depending, in part, on the network system employed, as should be apparent to one of skill in the art. In any case, an alarm indicator 208 appears over the corresponding instrument selection button 206. The alarm message received from the instrument includes a description of the nature of the alarm and different color indicators 208 may be used to distinguish between different alarms, for example, yellow for a warning, such as when a reagent is low, and red for an emergency, such as when the reagent is empty.

Figure 7:
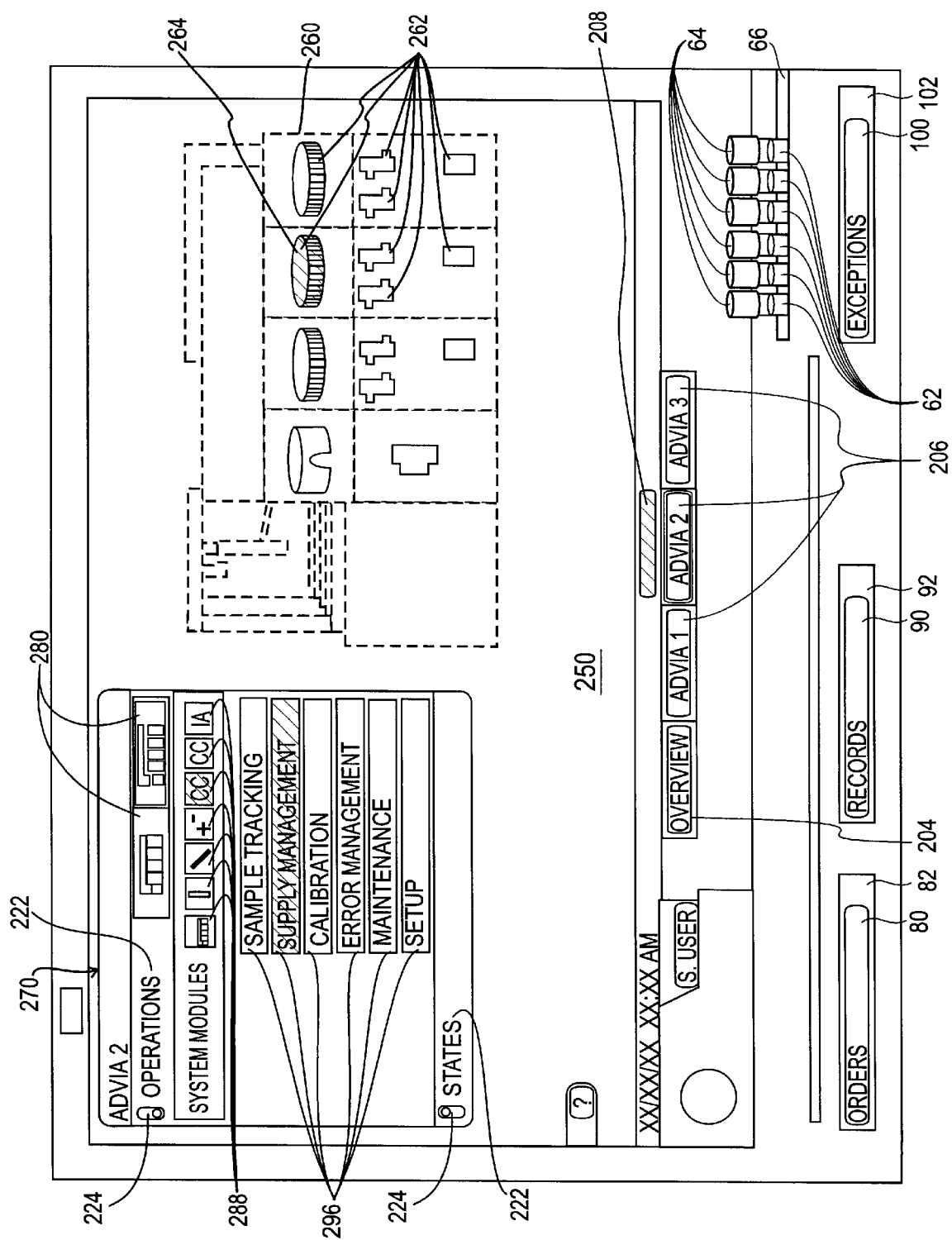
FIG. 7 is an illustration of the main screen of the GUI of the present invention with the instrument specific display in component view mode in the system management window showing an alarm condition.

If an alarm occurs when none of the instrument selection buttons 202 are engaged, or when the overview button 204 is not engaged and there were no previous alarms, the system automatically switches to the instrument specific display 250 for the affected instrument, as shown in FIG. 7. If multiple alarms occur at the same time, or if an instrument specific display 250 is already selected when an alarm occurs for a different instrument, the indicators 208 above the affected instrument selection buttons 202 are activated, however, the system does not automatically switch to the instrument specific display 250. Instead, the user must select which alarm to respond to and manually switch displays.

Figure 8:
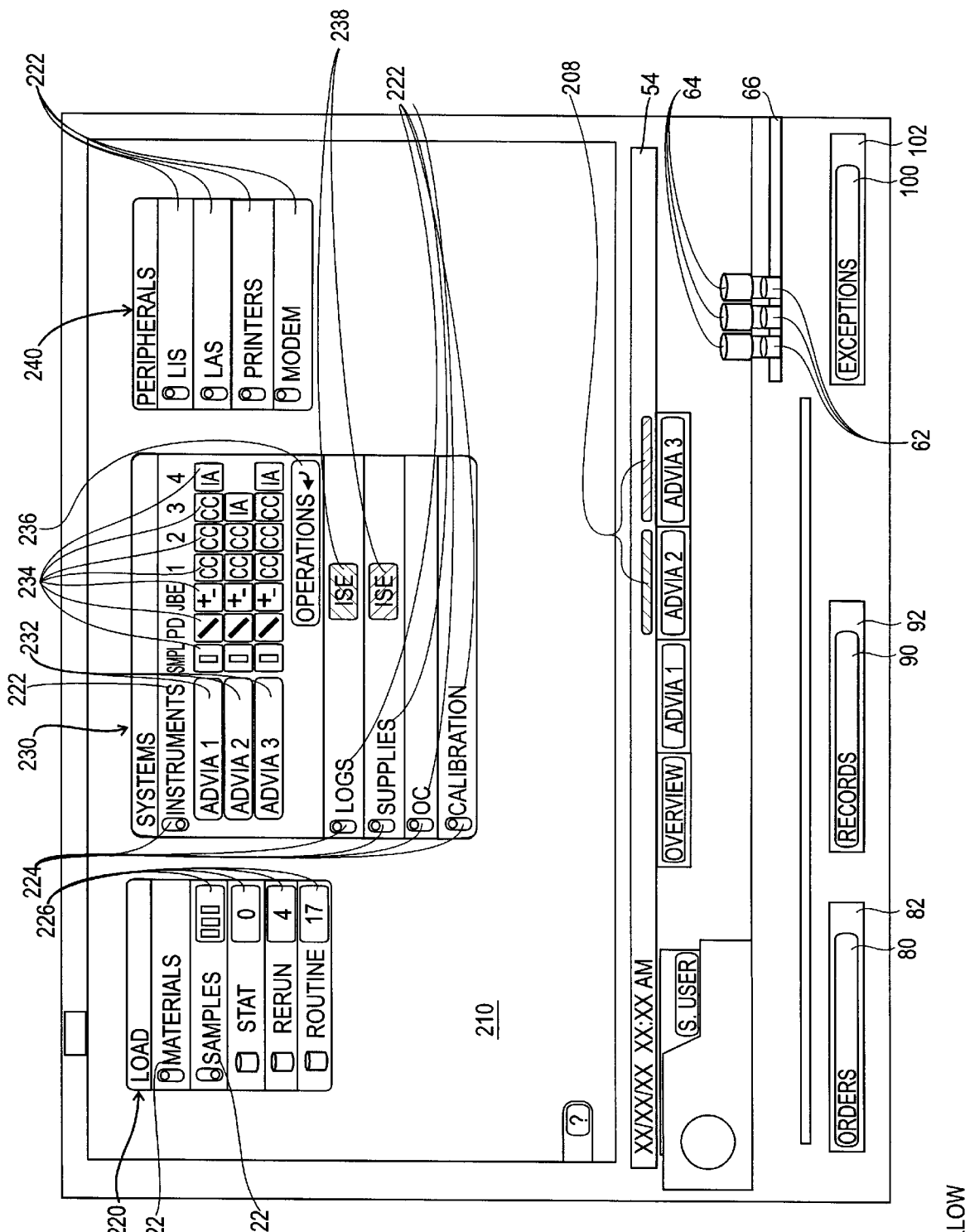
FIG. 8 is an illustration of the main screen of the GUI of the present invention with the overview display showing multiple alarm conditions.

Provided an instrument specific display 250 was not already engaged, the overview display 210 would indicate multiple alarms by appropriately colored indicators 238 placed to communicate the location and type of problem, for example, next to the section title, as shown in FIG. 8. In this example, there is an emergency condition relating to the logs in one of the ISE modules, and there is a warning condition relating to supplies in one of the ISE modules. By engaging the toggle switch 224 for the Logs section or the Supplies section of the Systems panel 230, that section is opened and the button corresponding to the affected component and/or instrument is backlit in the appropriate alarm color. Then, by clicking on the appropriate button(s), the user can be provided with detailed information regarding the problem and/or appropriate corrective measures. Alternatively, noting that alarm indicators 208 have appeared above the Advia 2 and Advia 3 instrument selection buttons 202, the user may activate one of the instrument specific displays 250 and proceed as described below.

Once switched to the instrument specific display 250, either manually or automatically, a graphical representation of the instrument 260 is depicted without its outer covering (skin) and all of the parts 262 that may be serviced by the operator, such as reagent carrousels, are illustrated. (See FIG. 7). Parts that require service technicians are not illustrated at the operator level in order to emphasize those that can be serviced by the operator. These parts requiring a service technician may, however, be illustrated under different conditions, for example, when a service technician logs onto the system using a special password. If the alarm relates to a part that can be serviced by the operator, the affected part 262 is highlighted, for example by a halo 264 colored to indicate the nature of the alarm (e.g., emergency or warning). In addition, the appropriate section of the Instrument panel 270 is also highlighted with the same alarm color.

Referring to FIG. 7, the display of an alarm condition is illustrated. An emergency (red) alarm indicator 208 has appeared over the Advia 2 instrument selection button 206 and the system has automatically engaged that button 206 to switch to the instrument specific display 250. The reagent carousel 262 of the second chemistry module has been highlighted 264 in red and the corresponding button 288 in the Operations section of the Instrument panel 270 has been highlighted. In addition, the button 288 for the affected component has been engaged, thereby producing a series of operation buttons 296 under the component buttons 288, with the operation button 296 relating to the alarm condition backlit in the appropriate color. The operator may now press the highlighted operation button 296 or the highlighted graphic 262 of the part to get more information about the alarm and/or be provided with directions for corrective action. The directions may include graphical displays, which aid in communicating the corrective action. It should also be noted that a user may, at any time, select any of the other parts of the instrument (either by clicking on the part 262 in the graphic display 260 or one of the component buttons 288 in the Instrument panel 270 and any of the associated operation buttons 296) to get information about the selected part.

The present invention, thus allows the operator to respond to common alarm states without special training or the need to memorize error messages and corresponding corrective actions. To further aid in calling the operator's attention to alarms, audible alerts produced by the PC speaker of the host computer may accompany the alarms and the alerts may differ, depending on the type of alarm. For example, a single or periodic beep may accompany warning alarms, while a constant high pitched tone may accompany emergency alarms. It should also be noted that while various methods of highlighting icons and/or data are described above (and throughout this description) to call the user's attention to a particular item, other well known methods of highlighting may be used, for example, highlighting, changing the color of a displayed item or its background and displaying text in bold, underlined or in a different font.

Data Management Desktop

The data management desktop 60 is the area of the GUI that contains access points for patient and control sample test results and data. In the illustrated embodiment, this data is organized into three data groups, Records, Orders and Exceptions. Each data group is accessed and displayed through "floating windows" 80, 90, 100 (similar to those found in the Microsoft Windows™ environment), which when not selected are displayed in corresponding slots 82, 92, 102 in the data management desktop 60 with the top title bar visible. If any of the above data groups are unavailable, either because there are none or because the particular user does not have access privileges, the corresponding floating window is dimmed and positioned deeper in its slot.

Figure 9B:
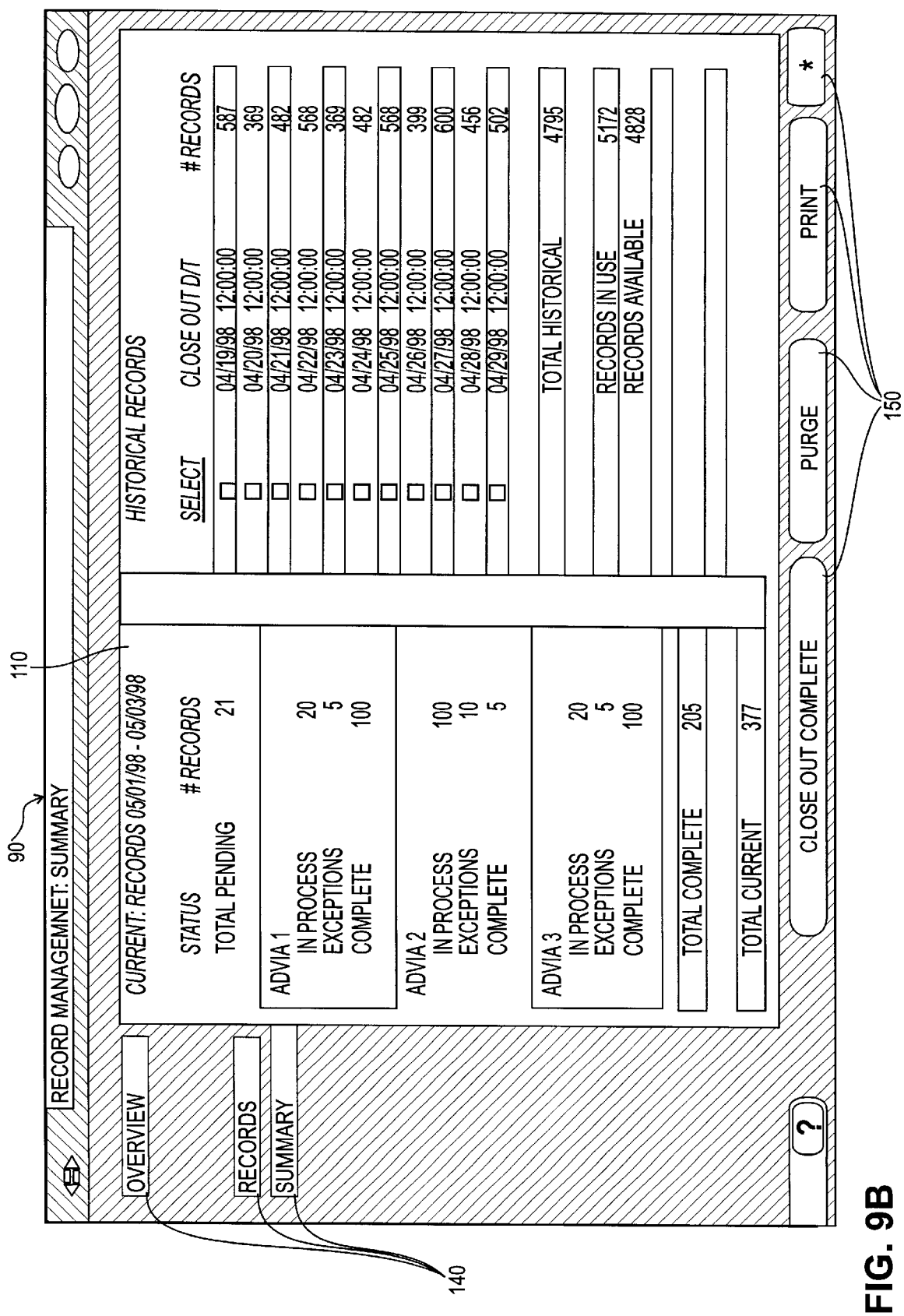
FIG. 9B is an illustration of the Records floating window display of the present invention with the Summary slide engaged.

The Records data group contains complete records for all patients. It contains biographical/demographic data, as well as results of tests already conducted and a record of tests to be performed. When the Records window 90 is selected, it emerges from its slot 92 and is displayed over the data management desktop 60 and system management window 200. (See FIG. 9A) The right side of the Records window 90 is a data region 110, which displays patient and quality control data and the left side has a number of user selectable slides 140, which control the data displayed in the data region 110. When a slide 140 is engaged, it is depicted as being connected to the data region 110 (e.g., the Overview slide in FIG. 9A). The slides 140 may be grouped in sets of mutually exclusive options or may be grouped in non-exclusive sets. Under the data region 110 are a number of command buttons 150.

The Overview and Details slides of the Records window 90 are mutually exclusive as are the Records and Summary slides. When the Overview and Records slides are engaged (this is the default shown in FIG. 9A), a list of patient records is displayed and the Pending, In Process, Exceptions and Complete slides (which are non-exclusive) may each be individually engaged to choose which records are included in the list.

The "By Work Order" and "Method:" slides are mutually exclusive and determine how the data is organized in the data region 110 when in overview format. When the By Work Order slide is engaged (this is the default), the results are displayed in overview format grouped by work order, as shown in FIG. 9A. When the Method slide is engaged, a menu appears from which the operator selects one or more methods. Once the desired method(s) is selected, the menu will close and the details by method screen is displayed. The operator can return to the overview screen by clicking the Overview slide.

When the Details slide is engaged, the details for selected record(s) replace the list of all records in the data region 110. The details screen is similar to the details screen of the Exceptions floating window 100, described below. In the details screen, the user may, depending on his or her access rights, modify, add or delete records. When the Summary slide is engaged (FIG. 9B), the overview or details screen of the patient data is replaced by the summary screen of all records. In this view, a summary of the status (e.g., in process, complete, exceptions) of all current records is displayed, by instrument, along with a summary of historical records.

The remaining slides (Composite, Search, Expand Rows, Sort By: and Filter) allow the user to search, sort and filter the displayed list as well as modify how certain fields are displayed. For example, when the Sort By slide is engaged the user is provided with a list of criteria by which the displayed data may be sorted. The user selects the desired sort criteria and the displayed data is sorted accordingly. The Expand Rows slide expands the data displayed for a record and the Composite slide displays information regarding multiple sample work orders. Additional slides 140 may be included to further control the sorting, filtering and display of data in the data region 110.

Figure 9C:
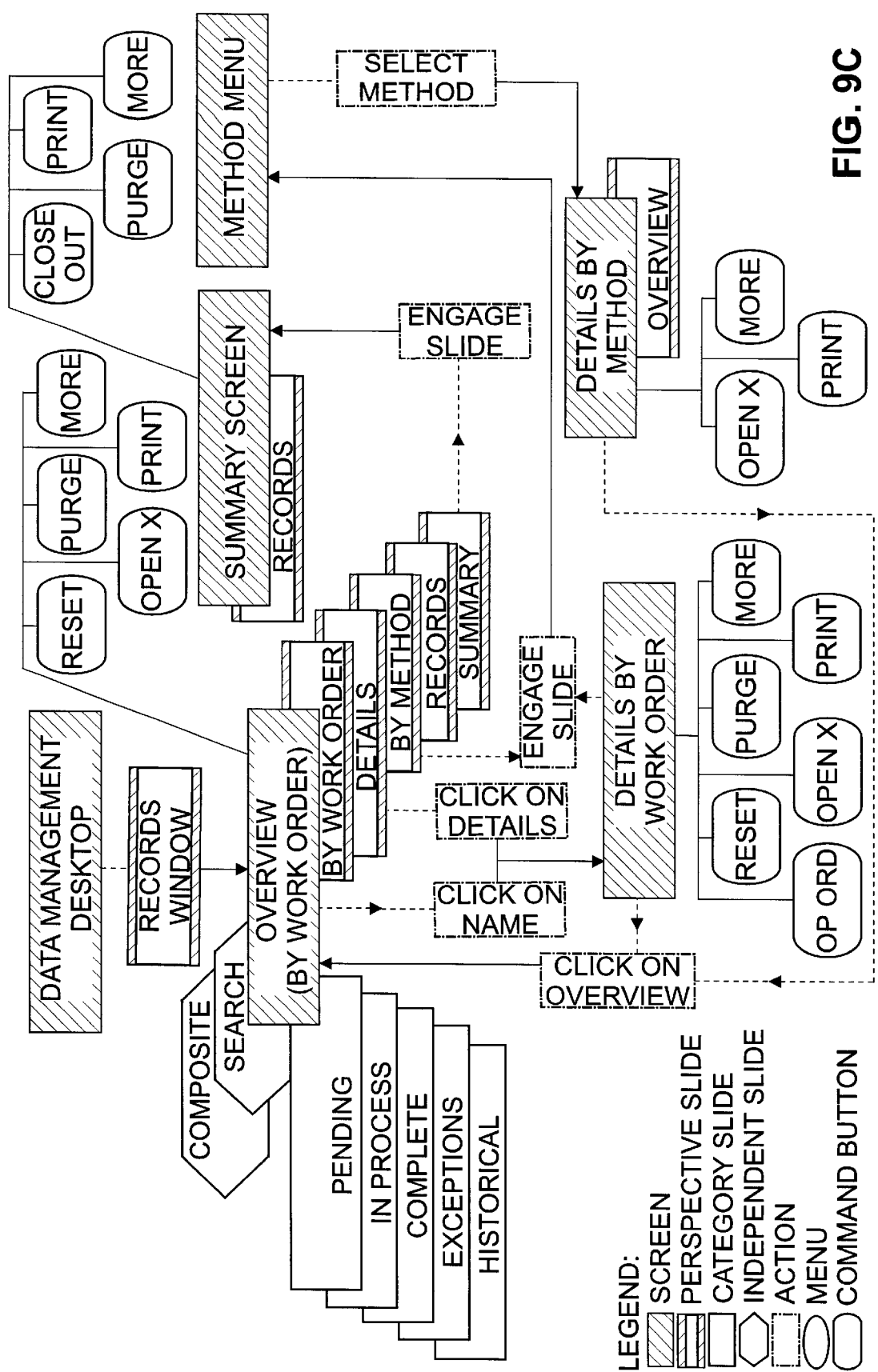
FIG. 9C is a flow diagram summarizing the navigation through, and options available in, the Records window of the present invention.

Under the data region 110 of the Records window 90 are a number of command buttons 150 which may or may not be available, depending on the data displayed and selections made by the operator. The operator my select one or more records in the Records window by checking the corresponding box(es) on the left side of the data region. Once at least one record has been selected, the operator may then print or purge the records by pushing the appropriate command button 150. The operator also has the option to reset records to a pending status or open the Exceptions window 100 (described below). The "*" command button is referred to as the "more" button and provides the operator with additional options, which may be less frequently used than those displayed or may simply not fit on the display screen due to size restraints. As with the slides 140, additional command buttons 150 may be provided to perform additional functions, as needed. FIG. 9C is a flow diagram summarizing the navigation through, and options available in, the Records window 90 using the command buttons 150 and slides 140.

The Orders data group is a sub-set of the Records group and contains all tests waiting to be conducted or that are in progress. For purposes of reporting, patient records are moved through the system as work orders. A work order consists of one or more samples, each with a unique sample id (SID), and a record of the tests to be performed on each sample, along with any required test parameters. By modifying work orders within the Orders data group, the user can modify the tests to be performed on samples that have not yet been processed. In addition, the user can create additional work orders for new tests. In the illustrated embodiment, work orders may be created either by downloading the information from the LIS or manually input through the keyboard. In addition, work orders may be individually created or batch processed from a common base, as described below, to simplify manual input.

Figure 10A:
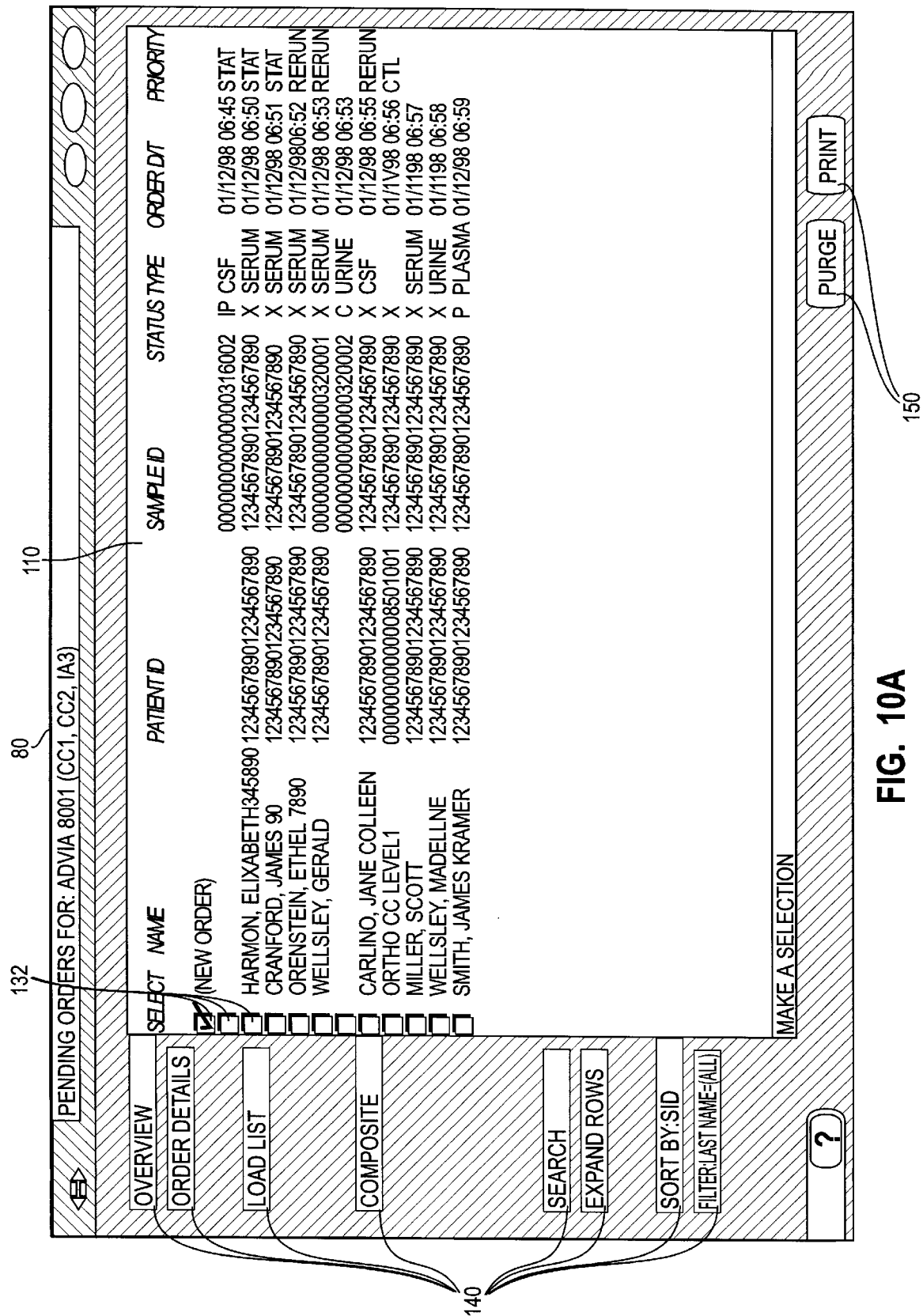
FIG. 10A is an illustration of the Orders floating window display of the present invention with the Overview slide engaged.
Figure 10B:
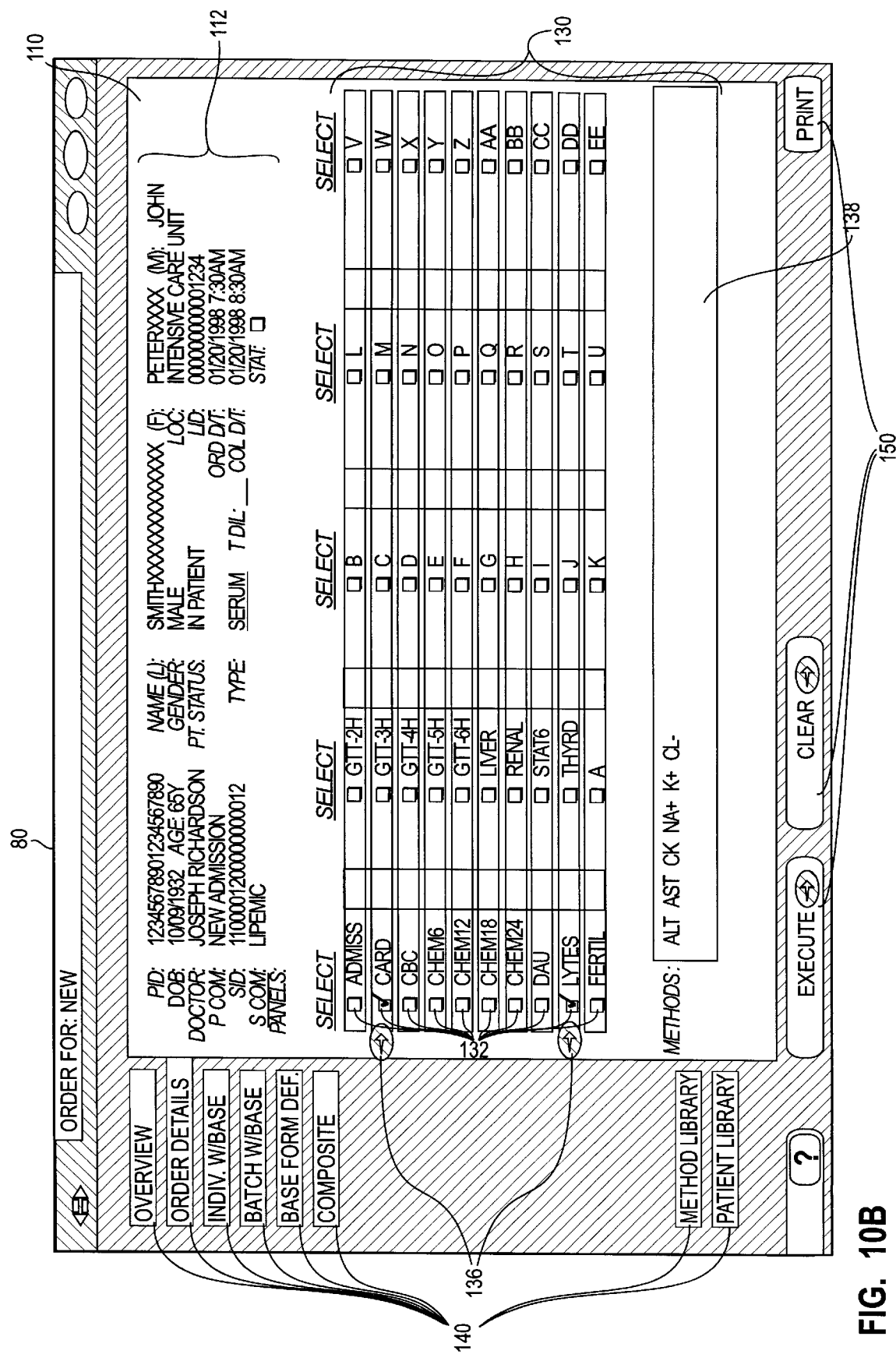
FIG. 10B is an illustration of the Orders floating window display of the present invention with the Details slide engaged.
Figure 10C:
FIG. 10C is an illustration of the Orders floating window display of the present invention with the Details slide engaged for a composite work order.

FIGS. 10A–10C illustrate the Orders floating window 80. Similar to the Records floating window 90, the Orders window 80 includes a data region 110, a number of slides 140 to control what is displayed within the data region 110 and a number of command buttons disposed below the data region 110, all of which function as previously described in connection with the Records window 90. When the Overview slide is engaged, a list of all pending work orders is displayed. This is the default shown in FIG. 10A. (Alternatively, the tests may be displayed by method). If the Load List slide is engaged, the list of pending orders is replaced by a list of all samples that must be loaded on the system.

Figure 11A:
FIG. 11 is an illustration of the Methods Library screen of the present invention.
FIG. 11B is a flow diagram summarizing the navigation through, and options available in, the Orders window of the present invention.

To edit an existing work order, the operator checks one of the boxes 132 to select the desired work order and engages the Details slide, which is mutually exclusive with the Overview slide. To create a new work order, the operator selects the "(New Order)" box 132 before engaging the Details slide. In the details view (FIG. 10B), the top portion 112 of the data region 110 contains patient demographic data and the bottom portion 130 contains a display of available panels of tests. By checking the appropriate boxes 132, the user specifies which test panels will be performed for the patient's sample(s). The selected panels are automatically translated by the system into the corresponding tests which are listed in the Methods field 138 in the bottom portion 130 of the data region 110. If multiple samples are included on a single work order, the data region 110 would include a separate Methods field for each sample (see FIG. 10C). If the operator wishes to select an individual test rather than an entire panel of tests, the Method Library slide may be engaged to display the method library 170, which is a complete list of all methods defined for the system (FIG. 11A). Numerous tests may be defined for a given system and additional tests may be defined by select users (as controlled by passwords etc.). In defining a method, the user is also able to define the classification of results (e.g., High/Low, Very High/Very Low and Panic High/Panic Low) as will be utilized in the exception review process, described below.

As an alternative to entering individual work orders from scratch, the operator may chose to create a base form from which individual, or several batched, work orders may be created. A base form is created by engaging the Base Form Def. slide when a new work order is displayed in the details view and entering/editing information to be included in the base form. For example, if one doctor ordered the same set of tests on multiple patients, the doctors name and the selected methods would be entered in the base form. Once the base form is created, disengaging the Base Form Def. slide will save the entries made as a template. The user may then engage the Indiv. W/Base on the details view of a new work order to enter an individual work order using this base form. Alternatively, the user could engage the Batch W/Base slide to enter multiple work orders using the same base form. If this slide is engaged, the system automatically increments the SID for each new work order.

Figure 11B:
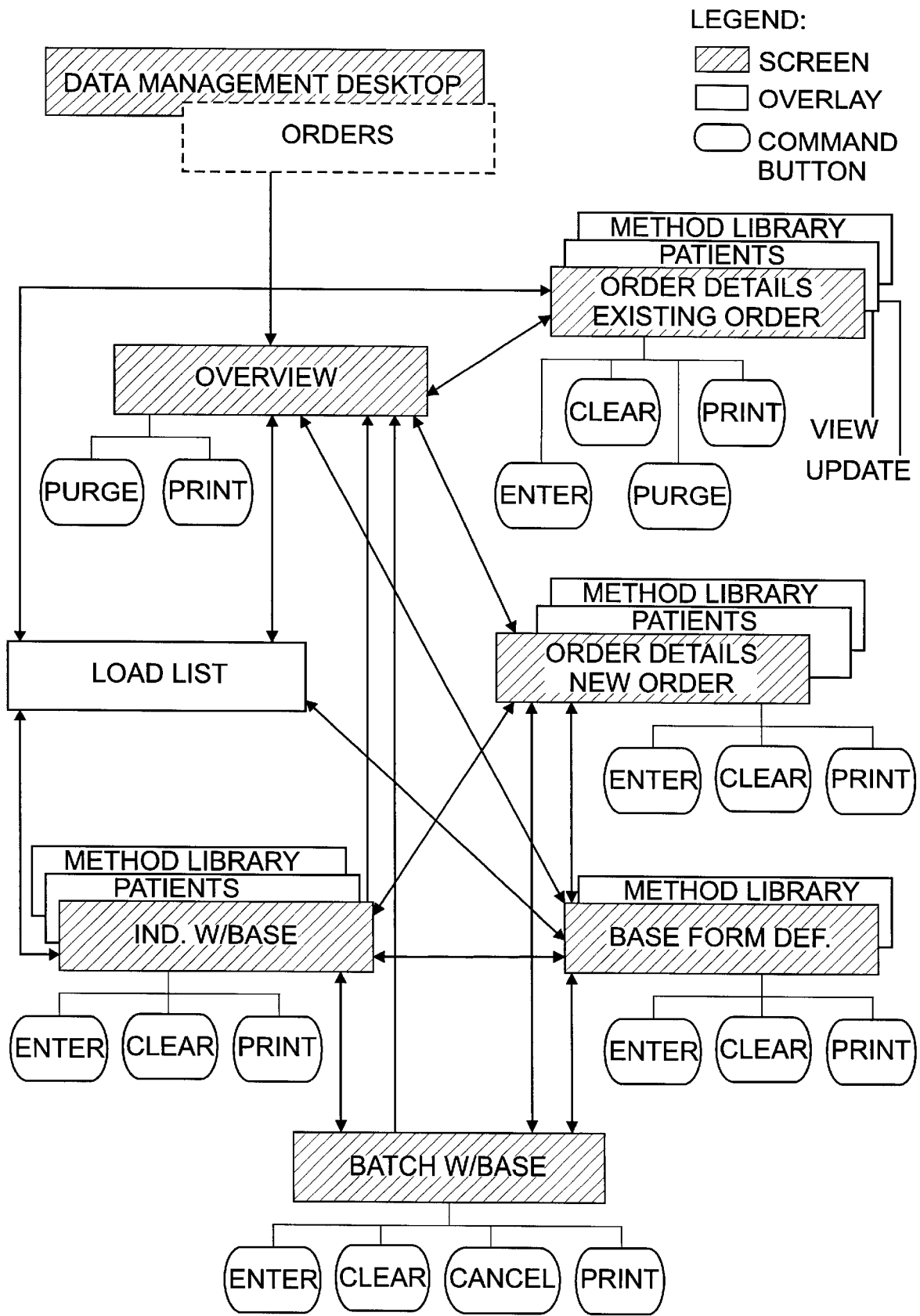

All entries on a new work order (and changed entries on an existing work order) are indicated by a user modified change arrow 136 (see e.g., FIG. 10B). Once the new work order is completed (or changes to an existing one are made), the Execute command button must be pressed for the system to accept the work order. Pressing the Clear command button clears all selections indicated by user modified change arrows 136. Pressing the Print command button prints the current work order. At this time, the system checks each selected method against the given sample type. If a method designated is for a sample type other than the one specified, the system automatically engages the Composite slide and opens a new Methods field 138 for that method or methods. The operator is then prompted to input information for this sample (see FIG. 10C). FIG. 11B is a flow diagram summarizing the navigation through, and options available in, the exceptions review process.

The Exceptions data group is also a sub-set of the Records data group and contains patient and quality control results, which violate user specified review conditions and, therefore, require review by the operator. The operator can update orders, edit records and/or validate results in the Exceptions group. The system automatically selects a default disposition for exceptions based on the user selected method definition parameters (described above) and exception review criteria and the ability to modify or create these parameters may be password restricted to a limited number of operators to ensure that consistent review criteria are employed. Once the system suggests a disposition, the operator can either accept the default disposition, or modify it.

FIG. 12 illustrates an example of an Exception Review Criteria Parameter definition screen. By checking the appropriate boxes 132, the user defines which results are included in the Exceptions data group for mandatory operator review and sets a default disposition for certain events. For example, in FIG. 12, the operator has required all "Very Hi/Low" results be reviewed as exceptions and all range failures be rerun automatically by checking the appropriate boxes 132. The user defines what is considered a "Very Hi/Low" result in the method definition section, as described above.

In addition to the Exceptions floating window 100, each exception test result is also represented graphically by a test tube icon 62, which appears in an exceptions channel 66 on the data management desktop 60. The test tube icons 62 have different color caps 64 to indicate the urgency and/or type of test results they represent. For example, white may indicate a routine sample, blue may indicate a rerun, yellow may indicate a quality control, red stripes may indicate a stat sample and glowing red may indicate an alert sample. The test tube icons 62 are ordered within the channel 66 according to priority (e.g. alert tubes first, stat tubes second) to ensure prompt attention where required. In this manner, the operator is notified immediately of test results and their urgency. The operator can then choose to review a particular result merely by clicking on the appropriate tube icon 62, which then activates the details view of the Exception floating window 100 (described below) for the selected result.

Figure 13:
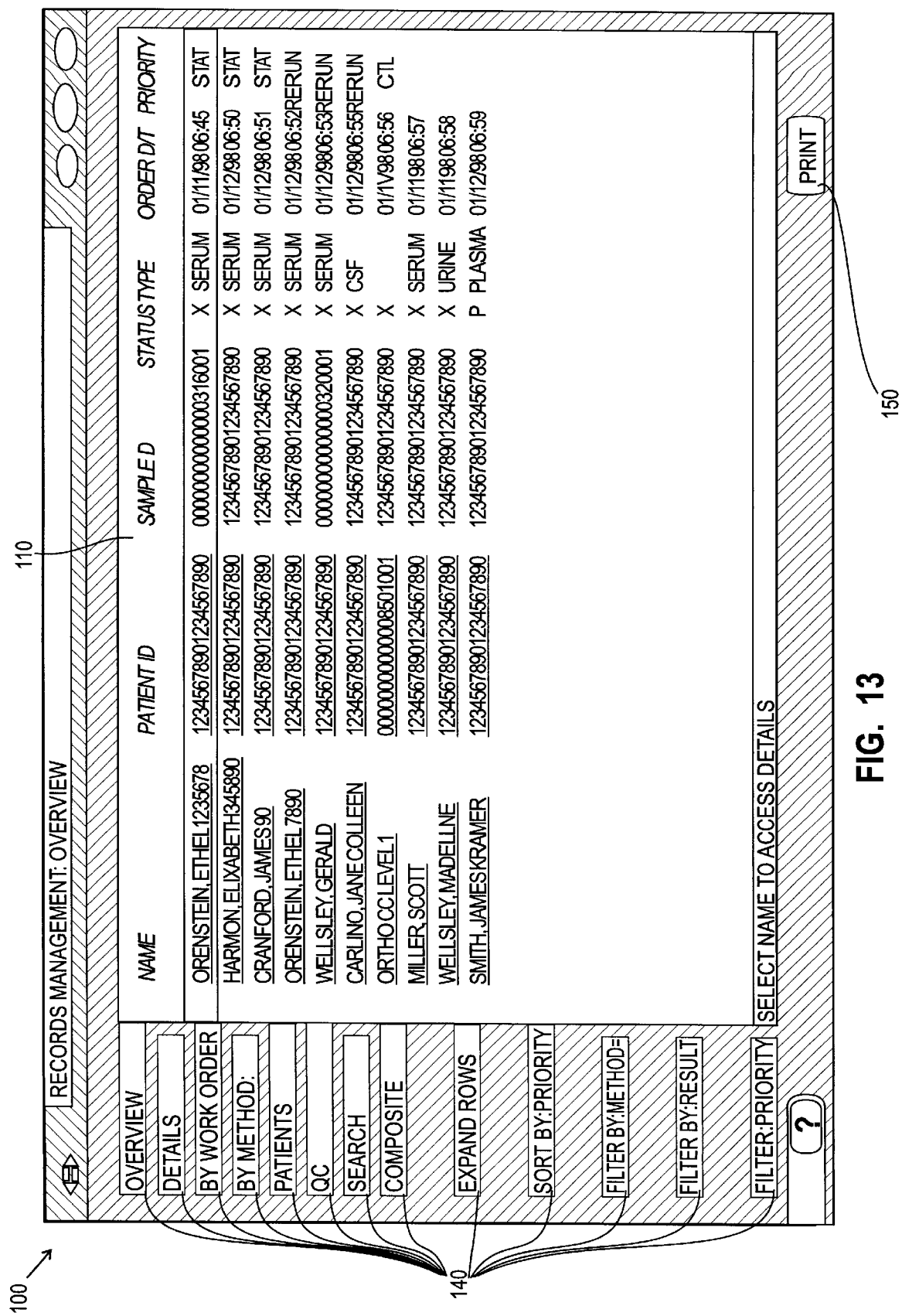
FIG. 13 is an illustration of the Exceptions floating window display of the present invention with the Overview slide engaged.

When the Exceptions window 100 is selected, it emerges from its slot 102 and is displayed over the data management desktop 60 and system management window 200 in a manner similar to the Orders and Records windows 80, 90. (See FIG. 13). The right side of the Exceptions window 100 is a data region 110 which displays patient and quality control sample results that must be dispositioned by the operator. The Exceptions window 100 also has a number of user selectable slides 140 on the left which control the data displayed in the data region 110. The first two slides, the Overview and Details slides, are mutually exclusive and determine what is displayed in the data region 110. When the Overview slide is engaged (this is the default), all of the selected exceptions are displayed in overview format as shown in FIG. 13. The Patients and QC slides select whether patient and/or quality control exceptions are displayed in the data region 110. These slides are non-exclusive.

Figure 14:
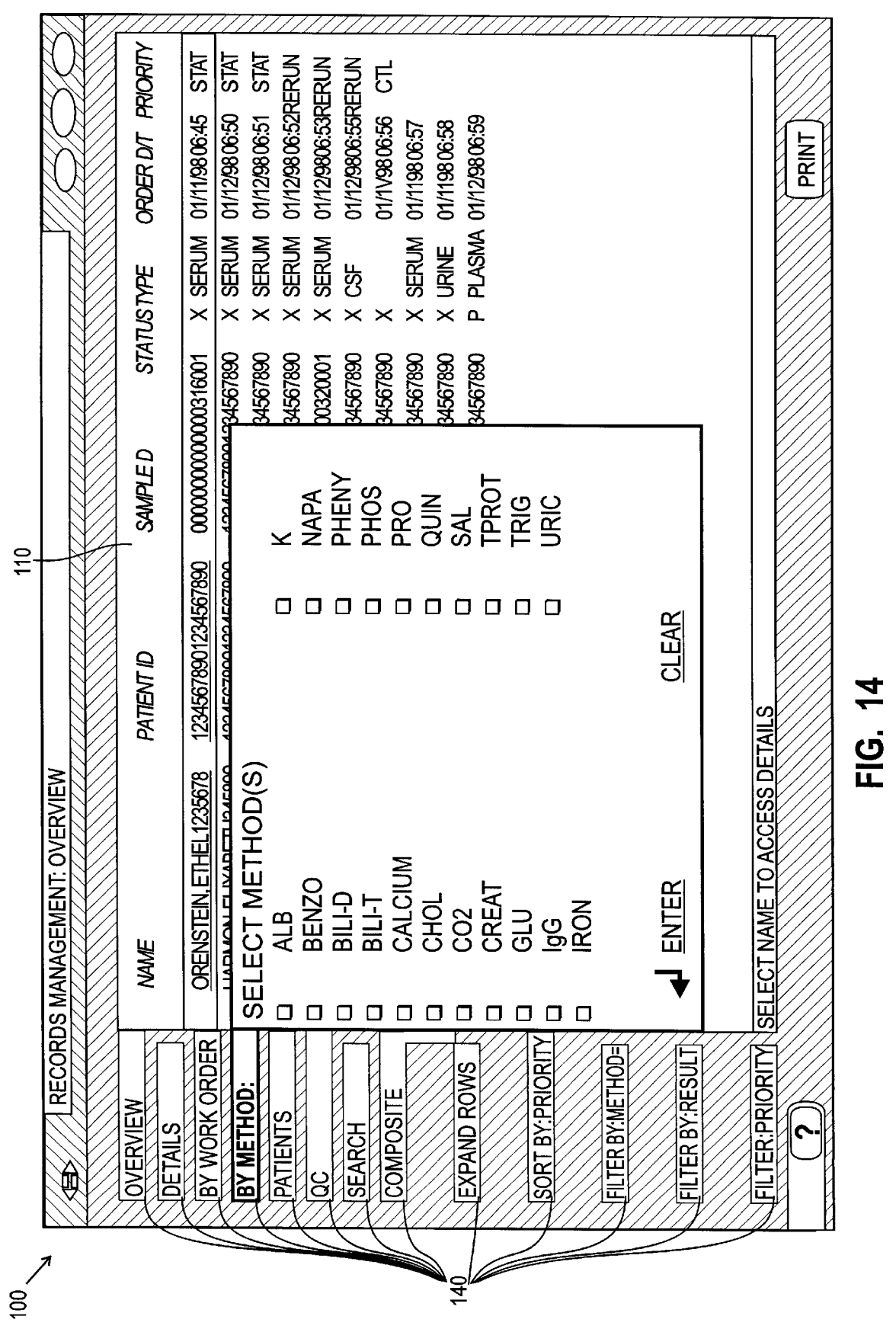

The "By Work Order" and "By Method:" slides are mutually exclusive and determine how the data is organized in the data region 110 when in overview format. When the By Work Order slide is engaged (this is the default), the results are displayed in overview format grouped by work order. (FIG. 13) When the By Method: slide is engaged, a menu appears (FIG. 14) from which the operator selects one or more methods. Once the desired method(s) is selected, the menu will close and the details by method screen is displayed. (FIG. 15) The operator can return to the overview screen by clicking the Overview slide.

Figure 16:
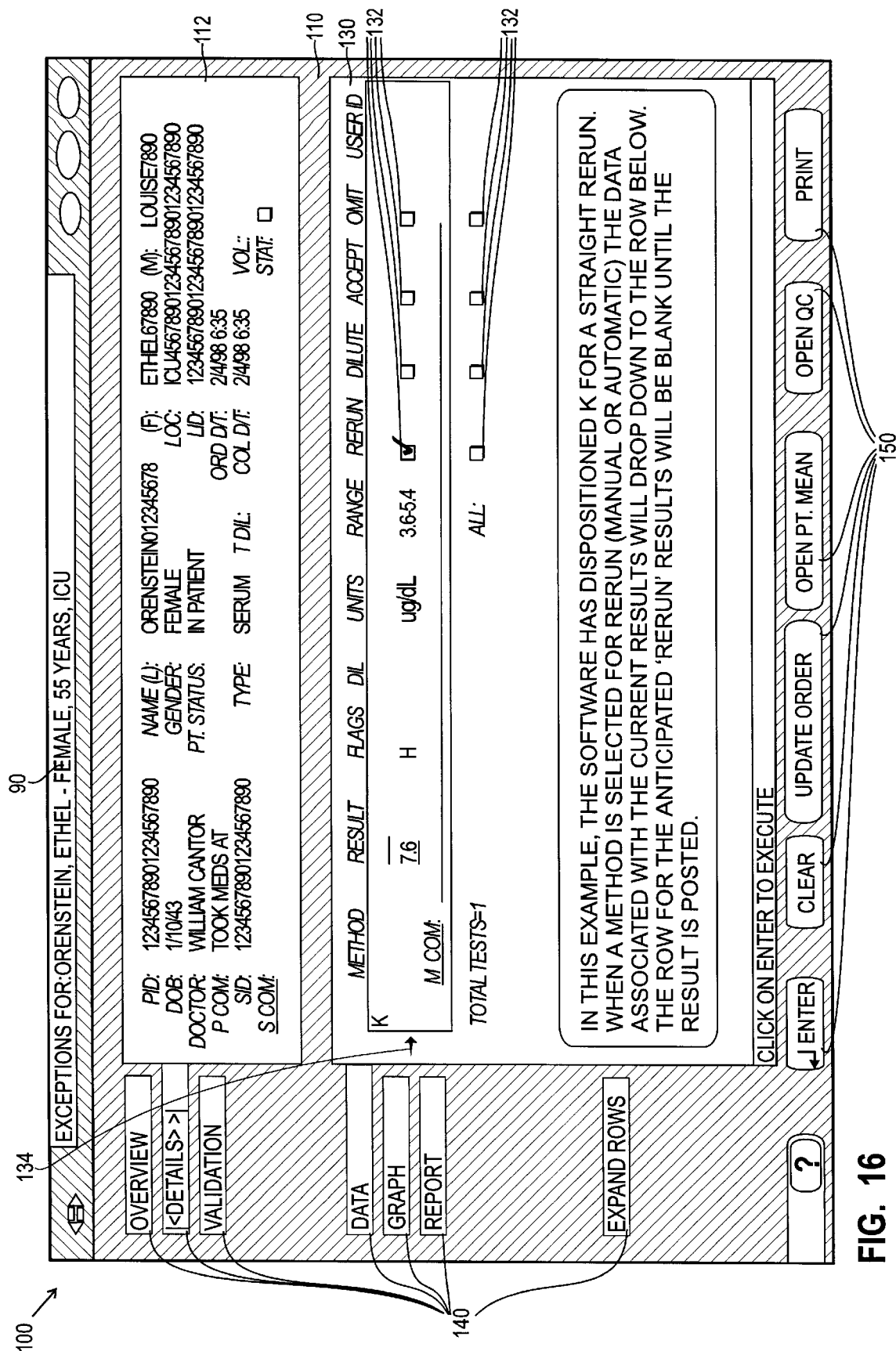
FIG. 16 is an illustration of the Exceptions floating window display of the present invention with the Details slide engaged.

When the Details slide is engaged, the details for a selected exception are displayed in details by work order format, as illustrated in FIG. 16, and the Overview slide is automatically disengaged. (This is the display entered when a specific exception tube icon 62 is selected from the data management desktop 60.) The top portion 112 of the data region 110 displays patient demographic data and the bottom portion 130 displays the details of the test results for the selected work order. The slides 140 available in the overview format are replaced. The Data, Graph and Report slides are mutually exclusive and control the form of the test result data displayed in the bottom portion 130 of the data region 110. FIG. 16 shows the Data slide engaged. When this slide is engaged, all methods and results for the associated sample (s) of the selected work order are displayed. By selecting a specific method and engaging the Graph slide, a graph of the selected method results will be displayed. If the Report slide is selected, results will be reported in a manner defined by the user.

With the Data slide engaged, test results are organized in rows. The first column of each row indicates the method for that row and the second column is the result. The results in the second column may be highlighted when appropriate, for example, backlit in red to indicate a "panic high" or "panic low" result and yellow to indicate a "very high" or "very low" result. The third column is the Flag column and has three sub-columns for Result, System and Validation flags. The following table summarizes the flags and their respective meanings:

TABLE 1

Data Display Flags

| | Flag | Meaning |
|---|---|---|
| Result Flags | PH | Panic High (result value backlit in red) |
| | VH | Very High (result value backlit in yellow) |
| | H | High (result value has yellow border) |
| | L | Low (result value has yellow border) |
| | VL | Very Low (result value backlit in yellow) |
| | PL | Panic Low (result value backlit in red) |
| | E | Edit Flag |
| | < | Result is less than lowest concentration used to determine the standard curve (result value backlit in red) |
| | > | Result is greater than highest concentration used to determine the standard curve (result value backlit in red) |
| System Flags | I | System Error (no result) |
| | R | Reagent Dispense Error (no result) |
| | S | Sample Dispense Error (no result) |
| | T | Temperature Error |
| | U | Replicate values used to calculate the results fail the imprecision limits (result not calculated) |
| Validation | Q | The QC sample run immediately prior to, or following the patients sample exceeds the acceptable SD range |
| | $\mu$ | The patient mean is outside the acceptable SD range |

TABLE 1-continued

Data Display Flags

| | Flag | Meaning |
|---|---|---|
| Flags | E | Patient result calculated by the system was modified by the user |
| | Δ | Calculated result has failed Delta Check (result value backlit in yellow) |

The Dil column is the dilution factor for the selected method, as stored with the order and applied when calculating the result. The Units and Range Columns indicate the units of measure and range for the results as defined for the particular method in the methods definition section described above.

The next four columns (also present when the Graph slide is engaged) control the disposition of the results and the last column is for the user id. Based on user defined disposition criteria, the system automatically selects a default disposition of the results, however, these can be manually modified by the operator by clicking the appropriate box(es) 132. To the left of each row, a change arrow 134 indicates that the system has suggested the action(s) indicated by checked boxes 132. If the operator modifies the system selected actions, a circle appears around the change arrow (a user modified change arrow) 136 to mark it as a user modified disposition. If Rerun or Dilute are selected for a result, an additional row will be added to the selected method on top of the existing one. Clicking on this additional row will allow for the selection of a rerun module and/or dilution factor as appropriate. Alternatively, all the methods within a sample may be batch dispositioned by clicking the appropriate "All" check box(es) 132 at the end of the methods list.

Figure 17:
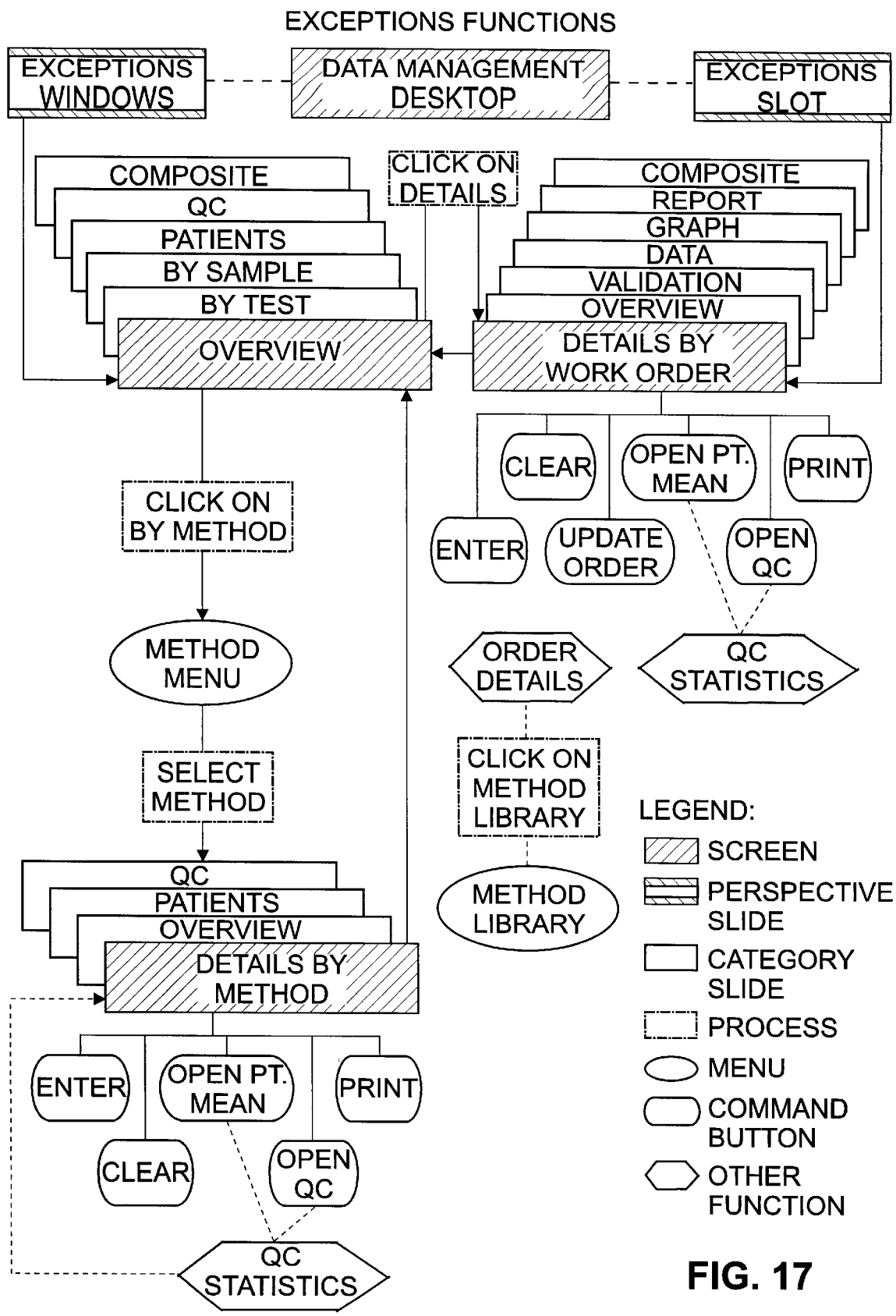
FIG. 17 is a flow diagram summarizing the navigation through, and options available in, the exceptions review process of the present invention.

The remaining slides (Search, Composite, Expand Rows, Sort By: and Filter By:) function as previously described for the Records floating window 90, above, and like the Records window 90, additional slides 140 may be included to further control the sorting, filtering and display of data. FIG. 17 is a flow diagram summarizing the navigation through, and options available in, the exceptions review process.

Under the data region 110 of the details display are a number of command buttons 150 which may or may not be available, depending on the data displayed and selections made by the operator. The Enter button is available whenever a change arrow 134, 136 is present and must be pressed to save any comments and store data marked by change arrows 134, 136. The Clear button is only available if the operator clicks any of the disposition check boxes 132 and a user modified change arrow 136 is present. The Clear button will reset a selected method [or all methods] to the system default, as defined by the user. The Update Order button is always available in the details by work order view. This button opens the order details screen, which allows the user to modify the original work order for the selected sample, for example, by adding additional methods or deleting methods not yet processed, as described above.

Figure 18:
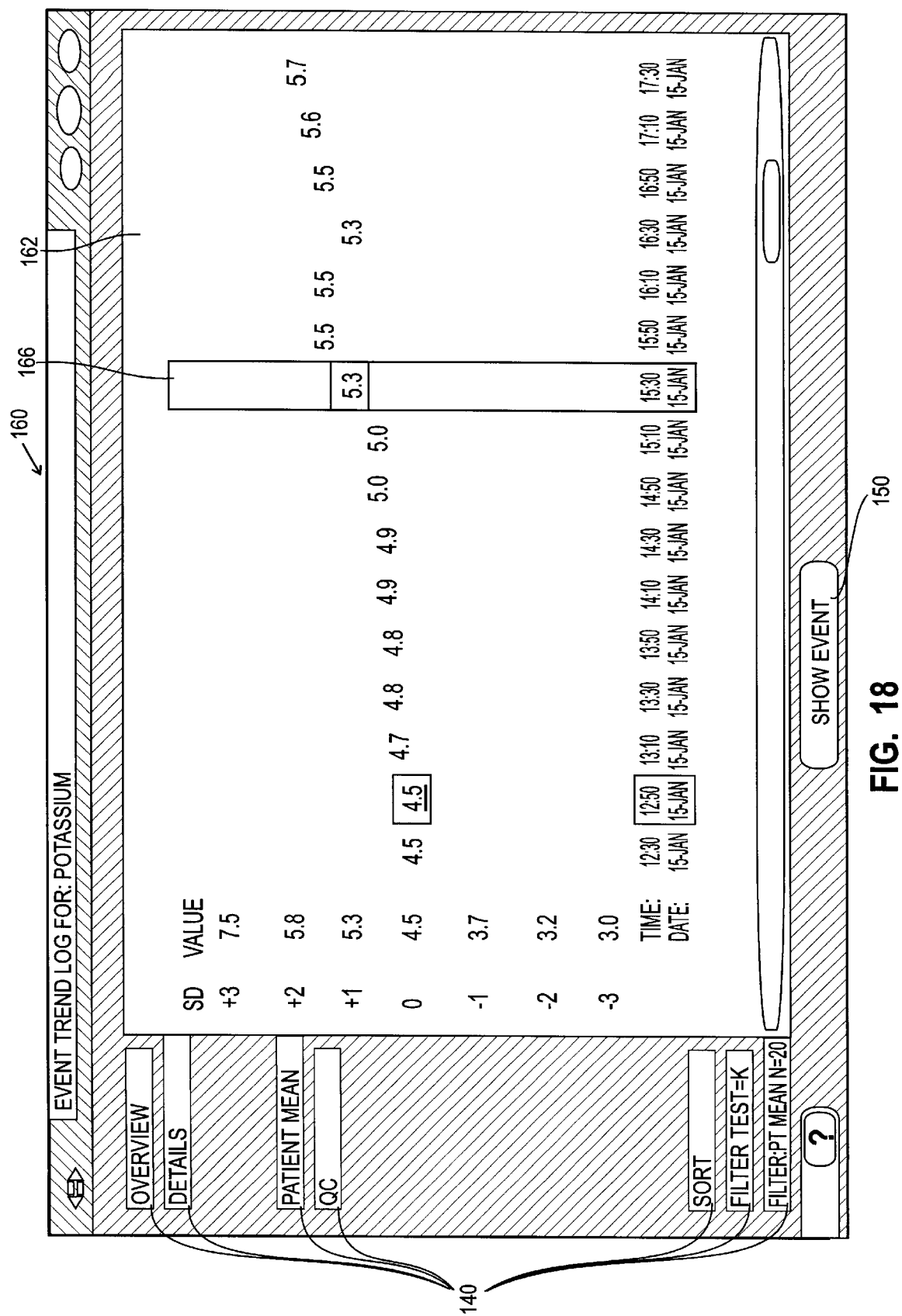
FIG. 18 is an illustration of the Event Trend floating window display of the present invention with the patient mean screen displayed.
Figure 19:
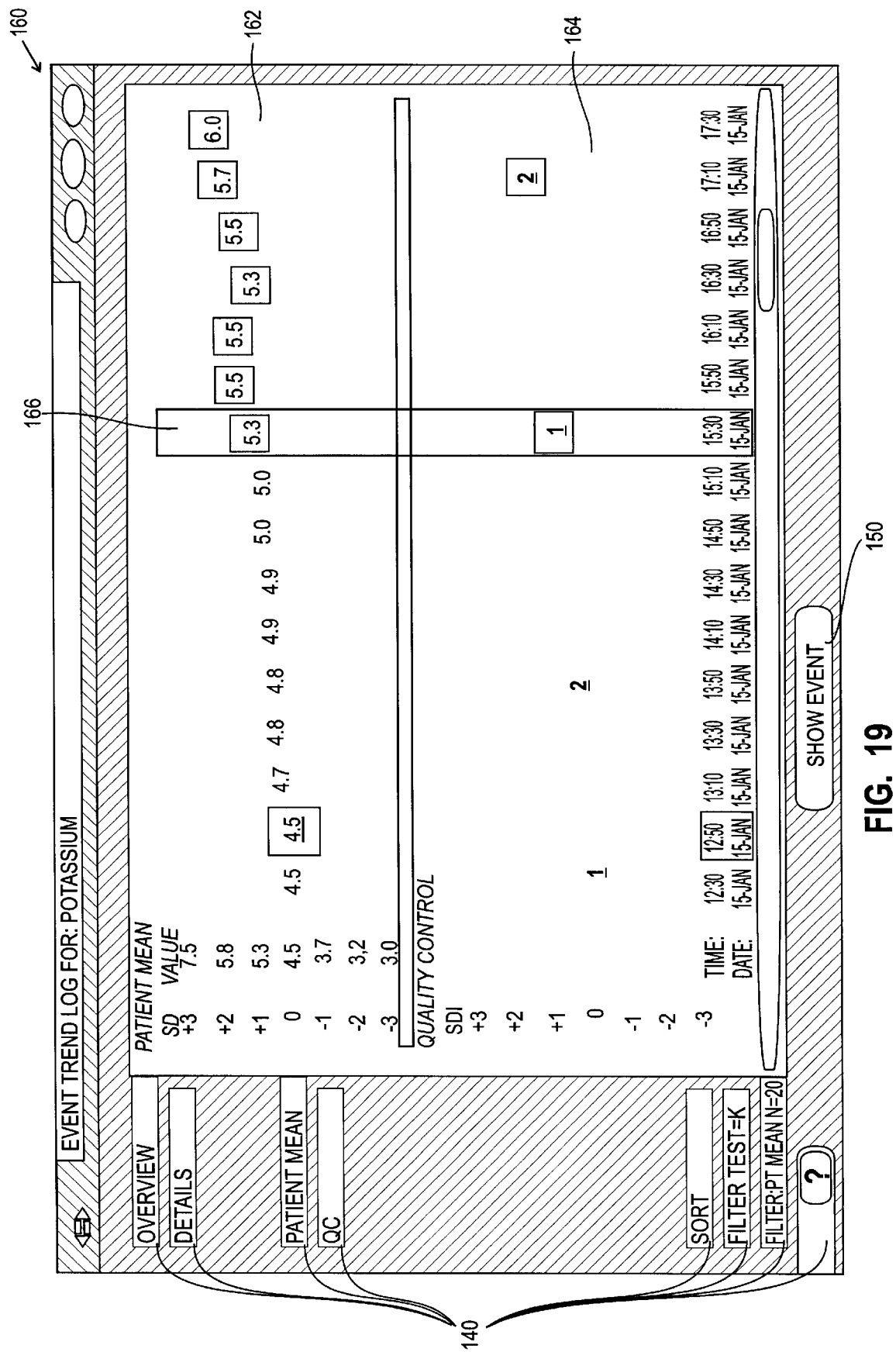
FIG. 19 is an illustration of the Event Trend floating window display of the present invention with the patient mean and QC screens displayed.

The Open Pt. Mean and Open QC buttons open the Event Trend window 160, which is displayed over the current exceptions screen. The Open Pt. Mean button causes the patient mean screen 162 to be displayed in the Event Trend window 160 and the open QC button causes the QC screen 164 to be displayed in the Event Trend window 160. Alternatively, the desired screen may be opened or closed from within the Event Trend window 160 by engaging or disengaging the corresponding slide. FIG. 18 illustrates the patient mean screen 162 and FIG. 19 illustrates both the patient mean and QC screens 162, 164 displayed simultaneously. The patient mean screen 162 and the QC screen 164 display patient mean data and QC data, respectively, for the selected system, module and method. In both cases, the data is plotted as a standard deviation from the mean against date and time. Any observation that coincides with a possible causative event (e.g., reagent change, calibration, reagent baseline, service or maintenance procedure) is highlighted and the corresponding values are underscored. In the illustrated embodiment, the events are highlighted by a vertical event bar 166. Clicking on the underscore will display the particular event and provide access to more details, if necessary, to ascertain if it is the cause for the problem being investigated. This greatly enhances the user's ability to review possible causes for a problem and reduces the time required for trouble shooting. Closing the Event Trend window 160 returns the user to the Exceptions window 100.

Figure 20:
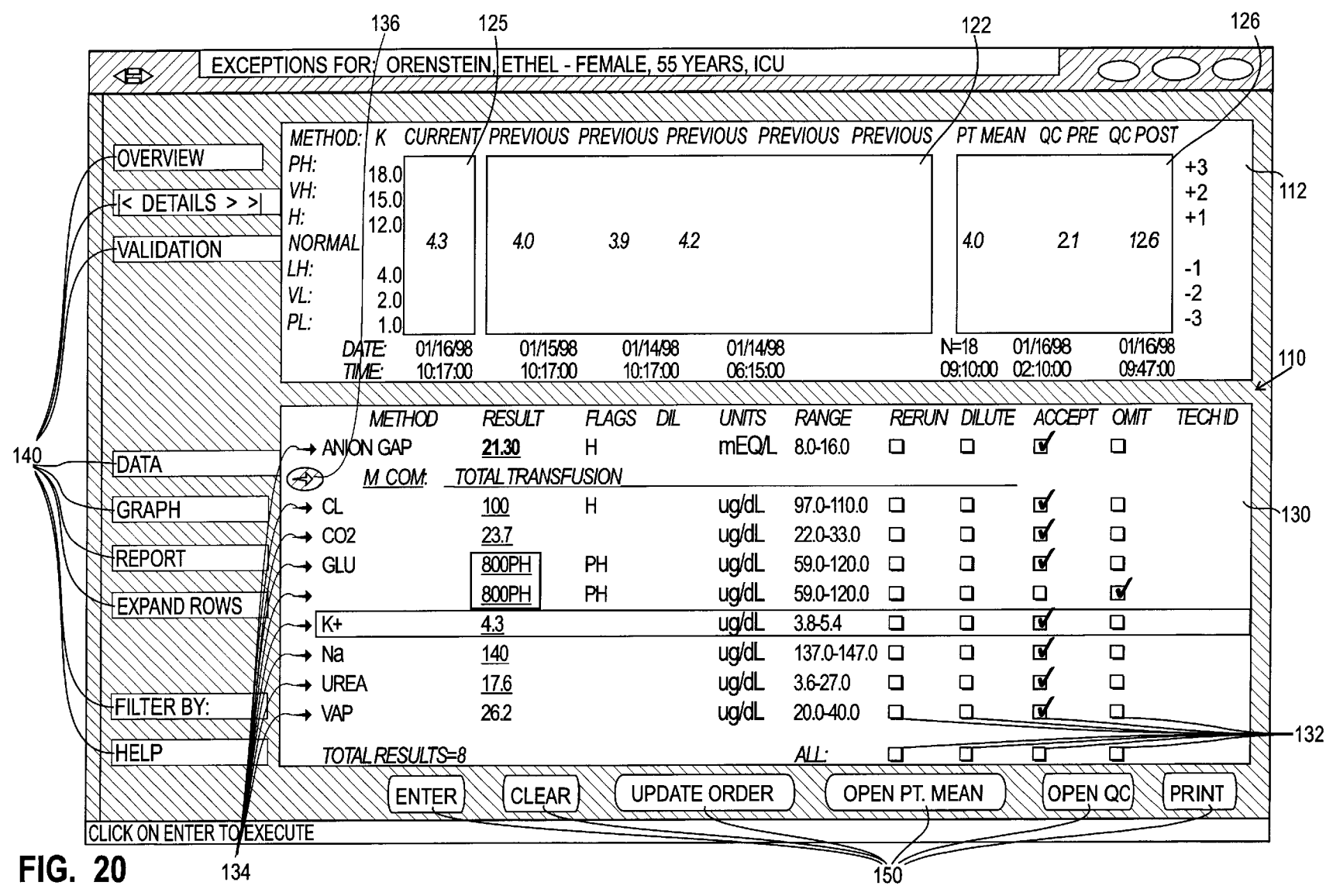

The Validation slide of the details display enables the operator to easily validate test results by providing the operator with a variety of information and tools. When the Validation slide is engaged, the patient demographic data in the top portion 112 of the data region 110 is replaced by validation data for the selected patient and method. The demographic data may be recalled simply by disengaging the Validation slide. As seen in FIG. 20, the validation data in the illustrated embodiment includes historical data stored for the patient (left side) and current QC data for the selected method (right side), however, other combinations of validation data may be used.

The historical data for the patient includes the current test result and up to the previous five results displayed in a patient data chart 122. The value for each result is displayed in an individual column with the date and time for each sample result displayed along the bottom of the patient data chart 122. Along the left side of the patient data chart 122 are marks for panic high (PH), very high (VH), high (H), normal, low (L), very low (VL) and panic low (PL) along with the corresponding ranges as defined for the selected method in the methods range definition section (described above). Each result is vertically positioned within the chart 122 according to its value. In addition, results may be highlighted to emphasize their value within the range. For example, panic high/low values may be backlit in red, very high/low values may be backlit in yellow and high/low values may have yellow border.

Using this chart 122, the operator may compare the current test results with the patient's historical results to aid in making a disposition decision for the current results. In addition, a "delta check" is performed by the system by comparing the change between the current result and the first previous result. If this change exceeds a user-defined value for the selected method, an indicator 125 may be provided to the operator (see FIG. 20).

The QC data for the selected method includes both patient mean data and quality control results, displayed in a QC chart 126. The first column of the chart 126 displays the value of the rolling patient mean for the selected method. This is the mean of the last N normal patients for this method run around the sample for the patient whose results are being reviewed. The numbers at the bottom of the column represent the total number of results (N=) and the time of the current test result. The next two columns display, respectively, the results of the last QC sample run before the current sample (QC Pre) and the next QC sample run after the current sample (QC Post), if available, for the selected method. Under these columns, the date and time of the corresponding QC result is displayed. To the right of the QC chart 126 is a scale representing the standard deviation. The QC data is positioned vertically within the chart 126 at a location to correspond to the standard deviation. As done elsewhere, results may be highlighted, or backlit, to emphasize certain results. For example, a value may be backlit in red if the standard deviation is greater than ±3.

Figure 15:
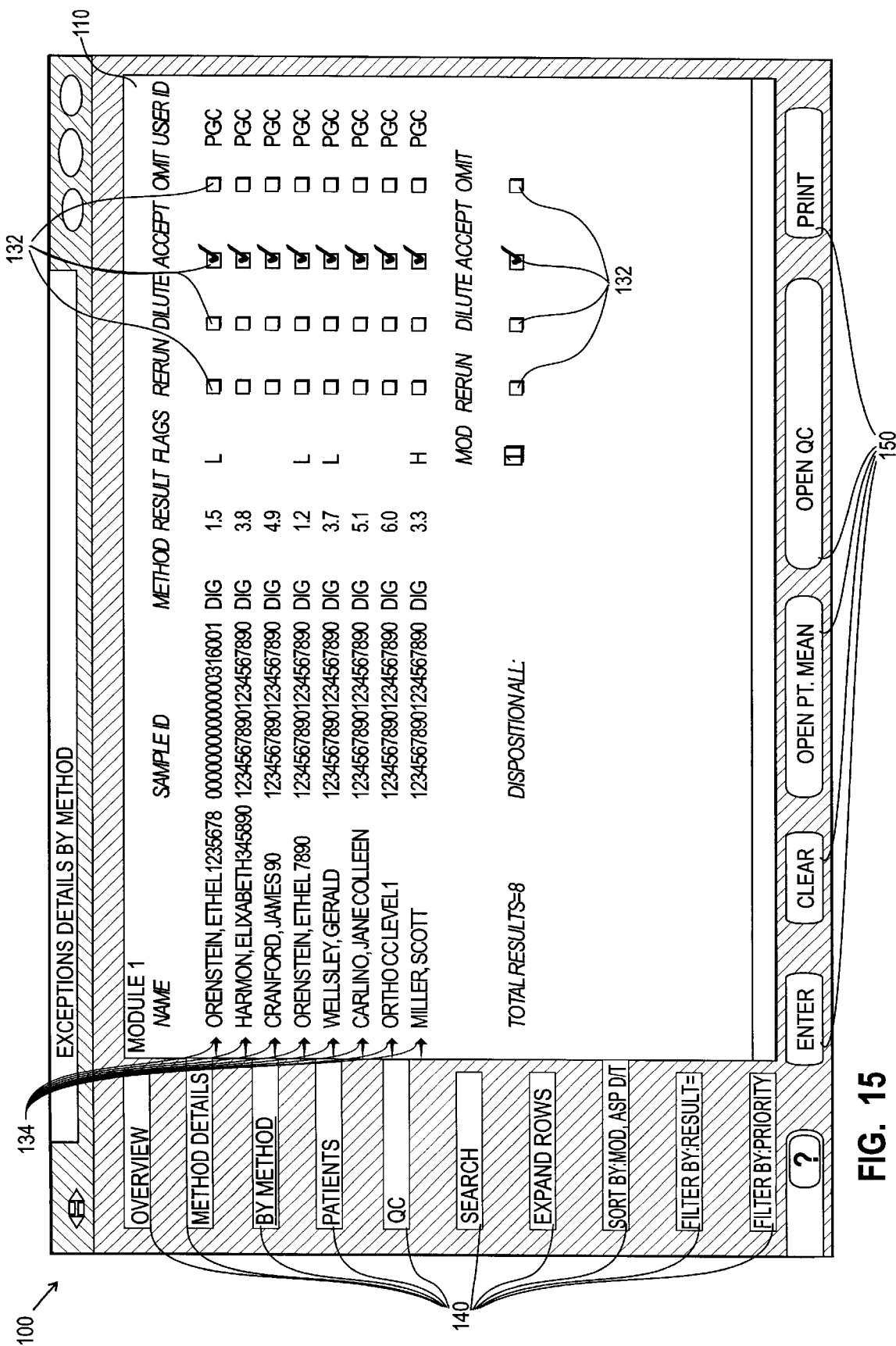
FIG. 15 is an illustration of the Exceptions floating window display of the present invention with the Method Details slide engaged.

Using the above information, the operator can decide on the disposition of a given exception. If more detailed validation data is desired, the Event Trend window 160 may be opened by clicking either the Open Pt. Mean or Open QC command button as described above. In the details by method screen, all results of a selected method are displayed, as illustrated in FIG. 15, with the slides 140 and command buttons 150 functioning as described in connection with the details by work order screen. Similarly, exceptions may be dispositioned and QC data may be checked as described above. If a particular exception is selected from the details by method screen, other methods on the same work order may be displayed.

The present invention has been described in terms of illustrated embodiments thereof. Other embodiments, features and variations within the scope of the appended claims will, given the benefit of this disclosure, occur to those having ordinary skill in the art.

What is claimed is:

1. A computer for use with a biomedical analyzer system having at least one biomedical analyzer instrument, said computer comprising:
   a microprocessor adapted to interface with said at least one instrument;
   a display linked to said microprocessor; and
   a data storage system linked to said microprocessor;
   wherein said computer is programmed to:
      control a state of said at least one instrument;
      enter a work order and store said work order in said data storage system, said work order including a sample id and at least one test id;
      send said work order to said instrument;
      receive test result data from said instrument and store said test result data in said data storage system;
      compare said test result data to a set of exception review criteria stored in said storage system to identify exception data; and
      display said exception data.

2. A user interface for a biomedical analyzer system having at least one biomedical analyzer instrument, said user interface comprising:
   means for controlling a state of said at least one instrument;
   means for entering a work order into a data storage system, said work order including a sample id and at least one test id;
   means for sending said work order to said instrument;
   means for receiving test result data from said instrument and storing said test result data in said data storage system;
   means for comparing said test result data to a set of exception review criteria stored in said data storage system to identify exception data; and
   means for displaying said exception data.

3. A computer for a biomedical analyzer system having at least one biomedical analyzer instrument, said computer comprising:
   a microprocessor adapted to interface with said at least one instrument;
   a display linked to said microprocessor; and
   a data storage system linked to said microprocessor;
   wherein said microprocessor is programmed to
      receive an alarm message from said at least one instrument, said alarm message identifying an alarm condition,
      automatically communicate said alarm condition to a user, and
      display a graphical image of said at least one instrument on the display.

4. A user interface for a biomedical analyzer system having at least one biomedical analyzer instrument, said user interface comprising:
   means to receive an alarm message from said at least one biomedical analyzer instrument, said alarm message identifying an alarm condition;
   means to automatically communicate said alarm condition to a user; and
   means to display a graphical representation which depicts said at least one biomedical instrument which is generating said alarm message in such a manner as to allow the user to immediately identify said at least one biomedical instrument generating said alarm message.

5. The user interface of claim 4 further comprising means to automatically display said instrument graphic image when said alarm message is received.

6. The user interface of claim 4 further comprising means to indicate a part of said instrument affected by said alarm condition.

7. The user interface of claim 6 further comprising means to provide a user with information regarding said affected part of said instrument.

8. The user interface of claim 4 further comprising means to display at least one part of said instrument wherein said at least one part may be serviced by an operator.

9. The user interface of claim 8 further comprising means to highlight said at least one part when said at least one part is affected by said alarm condition.

10. A computer for a biomedical analyzer system having at least two biomedical analyzer instruments, said computer comprising:
    a microprocessor adapted to interface with said at least two instruments;
    a display linked to said microprocessor; and
    a data storage system linked to said microprocessor;
    wherein said microprocessor is programmed to
       display an instrument specific display of a selected one of said at least two instruments, said instrument specific display including a graphical image of said selected instrument and an instrument control panel,
       display an overview display of said at least two instruments on said display, said overview display including means to control said at least two instruments, and
       selectively switch between said overview display and said instrument specific display.

11. A user interface for a biomedical analyzer system having at least two biomedical analyzer instruments, said user interface comprising:
    means to display an instrument specific display of a selected one of said at least two instruments, said instrument specific display including a graphical image of said selected instrument and means to control said selected instrument;
    means to display an overview display of said at least two instruments, said overview display including means to control said at least two instruments; and means to selectively switch between said overview display and said instrument specific display.

12. The user interface of claim 11 wherein said means to control said selected instrument comprises an instrument control panel in said instrument specific display.

13. The user interface of claim 11 further comprising means for displaying a plurality of patient records.

14. The user interface of claim 13 wherein said patient records comprise work orders and exception data.

15. A computer for a biomedical analyzer system having at least one biomedical analyzer instrument, said instrument having at least two components, said computer comprising:
   a microprocessor adapted to interface with said at least one instrument;
   a display linked to said microprocessor; and
   a data storage system linked to said microprocessor;
   wherein said microprocessor is programmed to
      provide a machine view for controlling said instrument, said machine view including means for controlling said at least two components at the same time,
      provide a component view for controlling said instrument, the component view including means for controlling said at least two components individually, and
      selectively switch between said machine and component views.

16. A user interface for a biomedical analyzer system having at least one biomedical analyzer instrument, said instrument having at least two components, said user interface comprising:
   a microprocessor adapted to interface with said at least one instrument;
   a display linked to said microprocessor;
   a data storage system linked to said microprocessor;
   a first means for controlling said at least one instrument, said first control means including means for controlling said at least two components at the same time;
   a second means for controlling said at least one instrument, said second control means including means for controlling said at least two components individually; and
   means for selecting between said first and said second control means.

17. The user interface of claim 16 wherein said first control means comprises at least one machine button and wherein said second control means comprises at least two component buttons.

18. The user interface of claim 17 wherein said machine and component buttons control a component state, said user interface further comprising a countdown timer to indicate a time remaining between a previous state and a selected state.

19. The user interface of claim 17 wherein said machine and component buttons control a component state, said user interface further comprising a progress bar adapted to extend between buttons to indicate the progress of components from a previous state to a selected state.

20. The user interface of claim 17 wherein said machine and component buttons control a component state, said user interface further comprising a means to selectively highlight said buttons to indicate a current state.

21. The user interface of claim 20 wherein said highlighting means comprises means to highlight portions of said at least one machine button to indicate the current sate of said at least two components individually.

22. The user interface of claim 17 further comprising means to highlight the machine and component buttons to indicate an alarm condition.

23. The user interface of claim 16 further comprising a status indicator for at least one of said at least two components.

24. A computer for a biomedical analyzer system having at least one biomedical analyzer instrument, said computer comprising:
   a microprocessor adapted to interface with said at least one instrument;
   a display linked to said microprocessor; and
   a data storage system linked to said microprocessor;
   wherein said microprocessor is programmed to
      gather validation data from said at least one instrument, store said validation data in said storage system,
      gather test result data from said at least one instrument,
      compare said test result data to a set of exception review criteria stored in said storage system to identify exception data, and
      compare said exception data to said validation data.

25. A user interface for a biomedical analyzer system having at least one biomedical analyzer instrument, said user interface comprising:
   a microprocessor adapted to interface with said at least one instrument;
   a display linked to said microprocessor;
   a data storage system linked to said microprocessor;
   means for gathering validation data from said at least one instrument and storing said validation data in said storage system;
   means for gathering test result data from said at least one instrument;
   means for comparing said test result data to a set of exception review criteria stored in said storage system to identify exception data; and
   means for comparing said exception data to said validation data.

26. The user interface of claim 25 wherein said validation data comprises historical patient data and QC data.

27. The user interface of claim 25 wherein said validation data comprises historical patient data.

28. The user interface of claim 25 wherein said validation data comprises patient test result mean data.

29. The user interface of claim 25 wherein said validation data comprises quality control test result data.

30. The user interface of claim 25 further comprising means for comparing said exception data to event trend data.

31. The user interface of claim 30 further comprising means for comparing said event trend data to at least one possible causative event.

32. The user interface of claim 30 further comprising means for comparing said exception data to at least one possible causative event.

33. The user interface of claim 25 wherein means for comparing said validation data and said exception data comprises means for displaying said validation data in a chart.

34. The user interface of claim 33 further comprising means for displaying a selected portion of said exception data in said chart.

35. The user interface of claim 25 further comprising means to display exception data on said display and highlight selected exception data according to predetermined criteria.

36. The user interface of claim 35 further comprising means to display validation data and highlight validation data according to predetermined criteria.

37. The user interface of claim 25 further comprising means to modify said exception review criteria.

38. A computer for a biomedical analyzer system having at least one biomedical analyzer instrument, said computer comprising:
   a microprocessor adapted to interface with said at least one instrument;
   a display linked to said microprocessor; and
   a data storage system linked to said microprocessor;
   wherein said microprocessor is programmed to
      gather test result data from said at least one instrument,
      compare said test result data to a set of exception review criteria stored in said storage system to identify exception data, and
      display at least one graphical icon representing said exception data.

39. A user interface for a biomedical analyzer system having at least one biomedical analyzer instrument, said user interface comprising:
   a microprocessor adapted to interface with said at least one instrument;
   a display linked to said microprocessor;
   a data storage system linked to said microprocessor;
   means for gathering test result data from said at least one instrument;
   means for comparing said test result data to a set of exception review criteria stored in said storage system to identify exception data; and
   means for displaying at least one graphical icon representing said exception data.

40. The user interface of claim 39 further comprising means for modifying said exception review criteria.

41. The user interface of claim 39 wherein said exception data comprises a plurality of exception work orders and wherein each exception work order is represented by an individual graphic icon.

42. The user interface of claim 41 wherein said plurality of exception work orders includes a first type of exception work orders and a second type of exception work orders, and wherein each said first type of exception work order is represented by a first graphic icon and said second type of exception work order is represented by a second graphic icon.

* * * * *